United States Patent
Binz et al.

(10) Patent No.: US 11,634,460 B2
(45) Date of Patent: Apr. 25, 2023

(54) NON-NEURONAL SNARE-CLEAVING BOTULINUM NEUROTOXINS

(71) Applicant: IPSEN BIOPHARM LIMITED, Wrexham (GB)

(72) Inventors: Thomas Binz, Wrexham (GB); Stefan Sikorra, Wrexham (GB)

(73) Assignee: IPSEN BIOPHARM LIMITED, Wrexham (GB)

( * ) Notice: Subject to any disclaimer, the term of this patent is extended or adjusted under 35 U.S.C. 154(b) by 0 days.

(21) Appl. No.: 16/754,844

(22) PCT Filed: Jan. 29, 2019

(86) PCT No.: PCT/EP2019/052146
§ 371 (c)(1),
(2) Date: Apr. 9, 2020

(87) PCT Pub. No.: WO2019/145577
PCT Pub. Date: Aug. 1, 2019

(65) Prior Publication Data
US 2020/0239528 A1    Jul. 30, 2020

(30) Foreign Application Priority Data
Jan. 29, 2018    (EP) .................... 18153941

(51) Int. Cl.
*A61K 38/48* (2006.01)
*C07K 14/33* (2006.01)
*A61K 38/00* (2006.01)

(52) U.S. Cl.
CPC .......... *C07K 14/33* (2013.01); *A61K 38/4893* (2013.01); *A61K 38/00* (2013.01)

(58) Field of Classification Search
None
See application file for complete search history.

(56) References Cited

U.S. PATENT DOCUMENTS

2013/0273590 A1 * 10/2013 Oyler .................. C12N 5/0618
435/219

FOREIGN PATENT DOCUMENTS

| WO | 2010120766 A1 | 10/2010 |
| WO | 2016025626 A2 | 2/2016 |
| WO | 2017035508 A1 | 3/2017 |

OTHER PUBLICATIONS

Seffernick et al. J. Bacteriol. 183: 2405-2410, 2001.*
Database Geneseq [online] Apr. 20, 2017 (Apr. 20, 2017), "Clostridium botulinum botulinum neurotoxin (BTx) D light chain, SEQ 25.", XP002789298, retrieved from EBI accession No. GSP:BDO42684 Database accession No. BDO42684.
Sikorra et al., J. Mol. Biol., 428:372-384 (2016).
Chen et al., PNAS, 106:9180-9184 (2009).
Masuyer et al., Annu. Rev. Pharmacol. Toxicol., 54:27-51 (2014).
International Search Report issued in PCT/EP2019/052146.
Written Opinion issued in PCT/EP2019/052146.
Examination Report, dated Aug. 28, 2020, in Australian Application No. 2019211190.
Extended European Search Report, dated Sep. 14, 2018, in European Application No. 18153941.2.

* cited by examiner

*Primary Examiner* — S. Devi
(74) *Attorney, Agent, or Firm* — Gene J. Yao; Barnes & Thornburg LLP

(57) ABSTRACT

The present invention provides a modified botulinum neurotoxin A (BoNT/A) L-chain protease that demonstrates enhanced cleaveage of human SNAP-23 (hSNAP-23) relative to unmodified (wild-type) BoNT/A L-chain protease, together with the use thereof for cleaving hSNAP-23.

18 Claims, 4 Drawing Sheets

Specification includes a Sequence Listing.

FIGURE 1A

| hSNAP23 binding sites | Point-mutations (in wt LC/A) | Fold increase hSNAP23 cleavage (vs wild type LC/A) | % hSNAP23 cleavage (at 1 μM LC/A, 20 μM hSNAP23) | $K_M$ [μM] | $k_{cat}$ [1/min] | % hSNAP25 cleavage (at 0.5 nM LC/A, 20 μM hSNAP25) |
|---|---|---|---|---|---|---|
| - | none (wild type LC/A) | 1.00 | 0.2 | 225±38 | 0.2 | 61±10 |
| P182/D178 | A308L | | | 79±20 | 0.09 | |
| P182/D178 | E148Y | 8.28 | 9.7 | 52± 6 | 0.36 | 29± 5 |
| P182/D178 | E148N | 1.18 | | | | |
| P182/D178 | T307F | | 1.6 | | | |
| P182/D178 | T307I | | 2.4 | | | |
| P182/D178 | Y312K | | 2.6 | | | 26± 2 |
| P182/D178 | Y312K, E148Y | | 1.7 | | | |
| P182/D178 | T307I, A308P, Y312V | 1.74 | | | | |
| P182/D178 | T307F, A308N, Y312L | 1.49 | | | | |
| P182/D178 | E148N, T307I, A308P, Y312V | 2.73 | | | | |
| P182/D178 | E148Y, T307F, A308N, Y312L | 2.01 | | | | |
| P182/D178 | E148Y, T307I, A308P, Y312V | 1.45 | | | | |
| P182/D178 | E148Y, T307L, A308T, Y312M | 2.23 | | | | |
| P182/D178 | E148Y, T307L, A308I, Y312M | 1.38 | | | | |
| K185 | V304D | | | 56±13 | 0.14 | |
| K185 | V304E | | | 65± 1 | 0.16 | |
| K185 | G305D | | | 52± 6 | 0.13 | 46± 3 |
| K185 | G305E | | | 61±12 | 0.12 | |
| R186 | S143D | | | 69±14 | 0.14 | 51± 3 |
| R186 | S143E | | | 57±11 | 0.13 | 102 ± 4.1 |
| R186 | S143Q | | | 91± 6 | 0.21 | |
| I198 | K166V | 1.096 | | | | |
| I198 | K166F | 1.66 | 66.1 | 44± 9 | 0.9 | 62± 8 |
| I198 | K166L | 1.43 | | | | 91± 6 |
| I198 | K166I | 1.098 | | | | 58± 1 |
| K206 | L256D | | 1.7 | | | 7± 2 |
| K206 | Y251D | | 2.3 | | | 8± 1 |
| K206 | Y251E | | 3.2 | | | 2± 1 |
| K206 | L256E, V258P | | | 173±42 | 0.19 | |

FIGURE 1B

| hSNAP23 binding sites | Point-mutations (in wt LC/A) | Fold increase hSNAP23 cleavage (vs LC/A-E148Y) | % hSNAP23 cleavage (% at 1 µM LC/A, 20 µM hSNAP23) [**% at 10 nM LC/A] | $K_M$ [µM] | $k_{cat}$ [1/min] | % hSNAP25 cleavage (at 0.5 nM LC/A, 20 µM hSNAP25) |
|---|---|---|---|---|---|---|
| *P182/D178* | *E148Y* | *1.00* | *9.7* | *52± 6* | *0.36* | *29± 5* |
| P182/D178, D189/D192 | E148Y, Q29A | 1.618 | 15.7 | | | 34± 7 |
| P182/D178, R186 | E148Y, S143E | 2.13 | 20.7 | | | 17± 3 |
| P182/D178,R186 | E148Y, S143D | 3.2 | 31.1 | | | 16± 4 |
| P182/D178, K185 | E148Y, G305D | 2.61 | 25.4 | 24 | 0.29 | 38± 3 |
| P182/D178, I198 | E148Y, K166F | | 5.6** | | | 28±10 |
| K185, I198 | G305D, K166F | | 3.8** | | | 66±14 |
| P182/D178, K206 | E148Y, Y251D | 1.298 | 12.6 | | | |
| P182/D178, D189/D192, K185 | E148Y, Q29A, G305D | 3.5 | 34.0 | 6.6± 1 | 0.28 | 38± 3 |
| P182/D178, D189/D192, R186 | E148Y, Q29A, S143D | 2.56 | 24.8 | 24± 4 | 17.7 | 23± 1 |
| P182/D178, I198, K185 | E148Y, K166F, G305D | | 15.2** | | | 60± 4 |
| P182/D178, I198, K185 | E148Y, K166V, G305D | 4.67 | 45.3 | | | |
| P182/D178, R186, K206, D189/D192 | E148Y, S143D, Q29A, Y251E | 1.36 | 13.2 | | | 2± 1 |
| P182/D178, D189/D192, I198, K185 | E148Y, Q29A, K166V, G305D | 6.422 | 62.3 | | | 41± 2 |
| P182/D178, D189/D192, I198 K185 | E148Y, Q29A, K166F, G305D | | 10.4** | 21± 1 | 13.4 | 40±14 |
| P182/D178, K206 | E148Y, L256D | | 5.8 | | | |
| P182/D178, K206 | E148Y, Y251E | | 9.0 | | | 3± 2 |
| P182/D178, R186, I198 | E148Y, S143D, K166F | | 18.2** | | | 11± 1 |
| P182/D178, I198, D210 | E148Y, K166F, S254A | | 13.3** | 19± 2 | 13.8 | |
| P182/D178, K185, I198, D210 | E148Y, K166F, S254A, G305D | | 29.9** | 16± 3 | 27.8 | |
| P182/D178, R186 | E148Y, S143Q | | 5.8 | | | 10± 1 |
| P182/D178, D168 | E148Y, K340H | | 3.5 | | | |

FIGURE 1C

| hSNAP23 binding sites | Point-mutations (in wt LC/A) | Fold change hSNAP23 cleavage (vs WT LC/A) | **% hSNAP23 cleavage (% at 1 μM LC/A, 20 μM hSNAP23) [% at 10 nM LC/A] | SNAP23 $K_M$ [μM] | $k_{cat}$ | % hSNAP25 cleavage v WT LC/A (at 0.5 nM LC/A, 20 μM hSNAP25) |
|---|---|---|---|---|---|---|
| *P182/D178* | E148R | 1.44 | | | | 4±2 |
| *P182/D178* | E148K | 0.84 | | | | 1.7 ±0.5 |
| R186 | S143D | 2.35 | | 69±14 | 8±2 | 72.6 ±4.9 |
| R186 | S143Q | 2.75 | | 91±6 | 13±1 | |
| K185 | V304D | 2.58 | | 56±13 | 8±1 | 82.9 ±8.4 |
| K185 | V304E | 1.46 | | 65±1 | 9±2 | |
| K206 | V258A | 0.59 | | | | 33.1 ±4.7 |

NON-NEURONAL SNARE-CLEAVING BOTULINUM NEUROTOXINS

CROSS-REFERENCE TO RELATED APPLICATIONS

This application is a U.S. national stage filing of International Patent Application No. PCT/EP2019/052146, filed Jan. 29, 2019, which claims the priority of European Application No. 18153941.2, filed Jan. 29, 2018.

REFERENCE TO SEQUENCE LISTING

The instant application contains a Sequence Listing that has been submitted electronically in ASCII format and is hereby incorporated by reference in its entirety. Said ASCII copy, created on Jul. 29, 2021, is named 79904-318569 SL.txt and is 21,004 bytes in size.

BACKGROUND OF THE INVENTION

Introduction

The present invention relates to a modified botulinum neurotoxin protease having the ability to cleave a non-neuronal SNARE protein, and to the use thereof for suppressing undesirable secretion from a mammalian cell by cleavage of said non-neuronal SNARE protein in said mammalian cell.

Toxins typically fall into one of two classes, namely cytotoxic toxins (e.g. plant toxin such as ricin) which kill their natural target cells, and non-cytotoxic toxins (e.g. botulinum neurotoxins) which do not kill their natural target cells. Non-cytotoxic toxins exert their effects on a target cell by inhibiting a cellular process other than protein synthesis.

Botulinum neurotoxin proteases act by proteolytically-cleaving intracellular transport proteins known as SNARE proteins (e.g. SNAP-25, VAMP, or Syntaxin). The acronym SNARE derives from the term Soluble NSF Attachment protein Receptor, where NSF means N-ethylmaleimide-Sensitive Factor. SNARE proteins are a large superfamily of proteins. An important function of SNARE proteins is to mediate the exocytosis of neurotransmitter molecules to the post-synaptic junction. SNARE proteins are therefore integral to secretion of molecules via vesicle transport from a cell.

*Clostridium botulinum* produces seven (A to G) different neurotoxins (BoNTs) which are differentiated serologically by the lack of anti-serum cross serotype neutralization. BoNTs elicit neuronal-specific flaccid paralysis by targeting neurons and cleaving neuron-specific SNARE proteins.

BoNTs have a 150 kDa polypeptide chain comprising a 100 kDa heavy chain and a 50 kDa light chain linked by a disulfide bond. BoNTs are organized into three functional domains: an N-terminal proteolytic light chain (L-chain); and a C-terminal heavy chain (H-chain), the latter consisting of a translocation domain ($H_N$) and a C-terminal neuron-binding domain ($H_C$). The toxic effect of BoNTs (nerve intoxification) follows a 3-step mechanism of action. First, the $H_C$ portion binds to a cholinergic nerve cell and becomes internalised via receptor-mediated endocytosis. Secondly, the $H_N$ portion translocates the L-chain across the endosomal membrane and into the cytosol of the nerve cell. Thirdly, the L-chain binds to and cleaves a neuronal SNARE protein within the cytosol, thereby suppressing neurotransmitter release from the nerve cell and resulting in nerve cell intoxication.

The seven BoNT serotypes cleave specific residues on one of three SNARE proteins:
serotypes B, D, F, and G cleave VAMP-2;
serotypes A and E cleave SNAP-25; and
serotype C cleaves SNAP-25 and syntaxin 1a.

Whilst native BoNTs are able to target and cleave neuronal SNARE isoforms such as VAMP-2, SNAP-25 and syntaxin 1a said proteases have little or no cleavage effect on the majority of non-neuronal SNARE proteins. This neuronal SNARE substrate specificity is consistent with and understood to be reflective of the natural neuronal cell binding specificity demonstrated by BoNTs. For example, BoNT/A cleaves human SNAP-25, but not human non-neuronal isoforms.

As early as 1989, BoNT/A was approved by the FDA to treat strabismus, blepharospasm, and hemifacial spasm and then for cervical dystonia, cosmetic use, glabellar facial lines and axillary hyperhidrosis. BoNT/A efficacy in dystonia and other disorders related to involuntary skeletal muscle activity, coupled with a satisfactory safety profile, has prompted empirical/ off-label use in a variety of secretions and pain and cosmetic disorders.

Clinical applications of BoNTs have focussed on targeting disorders associated with neuromuscular activity. More recently, pioneering research lead by Syntaxin Ltd has allowed the design of re-targeted BoNTs that bind to unique subset of neurons (e.g. nociceptive afferents—see WO96/33273, which is hereby incorporated in its entirety) and/ or to non-neuronal cells (e.g. airway epithelium cells—see WO00/10598, which is hereby incorporated in its entirety). This technology, known as Targeted Secretion Inhibitor (TSI) technology, involves replacement of the native BoNT binding domain by a different targeting moiety (e.g. a growth factor or other signalling molecule), and has opened the door for new BoNT-based therapeutics and therapies.

However, the selective cleavage of neuronal specific SNARE proteins by BoNTs has limited development of novel therapies in these non-neuronal systems. Neuronal and non-neuronal SNARE proteins are believed to be of equal importance to the process of intracellular vesicle fusion, and thus to the secretion of molecules via vesicle transport from a cell. Accordingly, the use of conventional BoNT-based therapeutics to inactivate neuronal SNARE protein driven secretion will not address any corresponding non-neuronal SNARE driven cellular secretion.

Accordingly, a need exists for an engineered BoNT L-chain protease that cleaves efficiently a non-neuronal SNARE protein.

SUMMARY OF THE INVENTION

The present invention solves one or more of the above problems by providing an engineered BoNT/A L-chain protease that cleaves a SNARE protein isoform that is mainly expressed in non-neuronal cells, namely human SNAP-23 (hSNAP-23). The present invention therefore provides a new class of non-cytotoxic therapeutic agent.

DETAILED DESCRIPTION OF THE INVENTION

Unless otherwise defined herein, scientific and technical terms used in connection with the present invention shall have the meanings that are commonly understood by those of ordinary skill in the art. Further, unless otherwise required by context, nomenclatures used herein, and techniques of cell and tissue culture are those well-known and commonly used in the art.

Nevertheless, with respect to the use of different terms throughout the current specification, the following definitions more particularly apply.

The singular terms "a", "an" or "the" encompass meaning plural meaning, such as "one or more", or "at least one", unless the context dictates otherwise.

The term "protease" means herein an enzyme, which is capable to hydrolytically cleave proteins and/or peptides. In the context of the present invention, said protease is more particularly a botulinum neurotoxin (BoNT) light-chain (L-chain) protease, i.e., a protease (also described as proteolytic domain) derived from botulinum neurotoxin, in particular from botulinum neurotoxin A (BoNT/A). As is well-known to the skilled practitioner, the light-chain of a botulinum neurotoxin provides a protease function (also known as non-cytotoxic protease function), and commonly has a molecular weight of about 50 kDa. Such non-cytotoxic proteases typically act by proteolytically cleaving intracellular transport proteins known as SNARE proteins (e.g. SNAP-25, VAMP, or Syntaxin)—see Gerald K (2002) "Cell and Molecular Biology" (4th edition) John Wiley & Sons, Inc. The naturally-occuring (i.e. wild-type) BoNT/A L-chain is more particularly capable to efficiently cleave SNAP-25, but is only de minimis capable of cleaving hSNAP-23 as further explained below. In contrast, the BoNT/A L-chain protease of the present invention, as described in more detail below, differs from the naturally-occuring BoNT/A L-chain in that it has an improved capacity to cleave hSNAP-23, and is referred herein as a "modified BoNT/A L-chain that cleaves hSNAP-23".

The capacity of cleaving hSNAP23 can be confirmed via a conventional assay, such as the assay described in Example 2 below. "Cleavage of hSNAP-23" more particularly means herein that the modified BoNT/A L-chain of the present invention demonstrates improved hSNAP-23 cleavage relative to the wild-type BoNT/A L-chain (SEQ ID NO: 1). Any simple comparative assay may be employed, such as the hSNAP-23 assay illustrated in Example 2. Wild-type BoNT/A L-chain is capable of only de minimis (i.e. background) hSNAP-23 cleavage.

Thus, a modified BoNT/A L-chain of the present invention demonstrates one or more (preferably both) of:
a) greater than 0.2% (for example greater than 0.5%, preferably greater than 1%, more preferably greater than 5%) hSNAP-23 cleavage in a cell-free assay (1 micromolar modified BoNT/A L-chain; 20 micromolar hSNAP-23; preferably incubated at about 37° C. for about 1 hour)—see Example 2, FIG. 1; and/ or
b) less than a Km of 225 (for example less than 200, preferably less than 150) micromolar in a cell-free assay (1 micromolar modified BoNT/A L-chain; 20 micromolar hSNAP-23; preferably incubated at about 37° C. for about 1 hour)—see Example 2, FIG. 1; and/or
c) less than a Kcat (1/min) of 0.2 (for example, less than 0.18, preferably less that 0.1) in a cell-free assay (1 micromolar modified BoNT/A L-chain; 20 micromolar hSNAP-23; preferably incubated at about 37° C. for about 1 hour)—see Example 2, FIG. 1.

The modified BoNT/A L-chain protease of the invention may optionally not only cleave hSNAP-23 but also SNAP-25. Cleavage of SNAP-25 can be confirmed via a conventional assay, such as the assay described in Example 3 below. According to this optional embodiment, "cleavage of SNAP-25" means herein that the modified BoNT/A L-chain of the present invention preferably demonstrates at least 0.5%, at least 1%, at least 2% preferably at least 3%, still preferably at least 10% SNAP-25 cleavage relative to the wild-type BoNT/A L-chain (SEQ ID NO: 1). Any simple comparative assay may be employed, such as the SNAP-25 assay illustrated in Example 3.

In a preferred embodiment, the modified BoNT/A L-chain protease of the invention cleaves hSNAP-23 but not SNAP-25, such as hSNAP-25.

The term "SNAP-23" (synaptosomal-associated protein 23) designates herein a SNARE protein which is capable of binding to various other SNARE proteins and of forming a high affinity complex with these proteins in a cell, preferably in a non-neuronal cell, thereby regulating intracellular cell membrane fusion in said cell. "hSNAP-23" refers more particularly to human SNAP-23, and preferably to the protein of sequence SEQ ID NO: 2.

The term "SNAP-25" (synaptosomal-associated protein 25) designates herein a SNARE protein which is capable of binding to various other SNARE proteins and of forming a high affinity complex in a cell, preferably in a neuronal cell, thereby regulating intracellular cell membrane fusion in said cell. "hSNAP-25" refers more particularly to human SNAP-25, and preferably to the protein of sequence SEQ ID NO: 3.

The term "modification", "change" or "mutation" can be used herein interchangeably, and refer to the alteration in the amino acid sequence compared to that of a protein of reference, i.e. herein relative to the wild-type BoNT/A L-chain (SEQ ID NO: 1). The amino acid sequence illustrated herein as SEQ ID NO: 1 is 438 amino acid residues in length and ends with K438. It is understood that K438 is the first lysine amino acid residue of the activation loop and most likely represents the C-terminal end of the L-chain after proteolytic cleavage of the activation loop. Thus, SEQ ID NO: 1 represents the (naturally) activated form of a wild-type BoNT/A L-chain. In this regard, prior to proteolytic activation, a wild-type BoNT/A L-chain is typically ~448 amino acid residues in length, which includes a short C-terminal extension of activation loop amino acid residues.

As further explained below, the present invention reveals the identification of critical amino acid positions within a wild-type BoNT/A L-chain that require rational change to a different amino acid residue in order to render a BoNT/A L-chain capable of hSNAP-23 cleavage. In this regard, introduction of an amino acid change (i.e. a mutation), may be effected by means of an amino acid insertion, a deletion or a substitution, and preferably by means of an amino acid substitution. Methods allowing introduction of such mutation are known to the skilled person in the art. For example, it is possible to introduce a mutation by random or directed mutagenesis, by PCR using degenerate primers, e.g. in the nucleotide sequence coding for the protein of reference. Said techniques are notably described by Sambrook et al. in "Molecular Cloning: A laboratory Manual", 4th edition, Cold Spring Harbor Laboratory Press, (2012, and updates from 2014), and by Ausubel et al. in "Current Protocols in Molecular Biology", John Wiley & Sons (2012).

The amino acid change occurs within one or more of the L-chain "binding pockets" relative to the wild-type BoNT/A L-chain (SEQ ID NO: 1). By "binding pocket", it is meant herein a region of the BoNT/A L-chain which comprises one or more amino acids which are the contact points (e.g. via hydrogen-bond, salt bridge, and/or hydrophobic contact) for binding to the corresponding binding site of hSNAP-23, and/or which provide the space to accommodate other substrate amino acid residue(s) (e.g. by modification, such as by substitution) capable to bind hSNAP-23. The term "binding to" as used herein means "suitable for binding to" and forms part of Applicant's rationale for the present invention—said rationale does not constitute an essential technical feature of the present invention. For example, the BoNT/A L-chain protease binding pocket defined by amino acid residues E148, T307, A308 and Y312 of SEQ ID NO: 1 refers to a region of the BoNT/A L-chain protease comprising amino acids E148, T307, A308 and/or Y312, and/or mutants thereof as described herein that Applicant believes cooperate to bind to a predicted binding site on hSNAP-23 (e.g. to the P182/D178 binding site of hSNAP-23).

The term "binding site" refers herein to a region of hSNAP-23 which comprises one or more amino acids that can be bound by the corresponding BoNT/A L-chain binding pocket. For example, the "P182/D178" binding site of hSNAP-23 comprises the amino acids P182 and/or D178 of hSNAP-23. The term "binding site" as used herein simply means "predicted binding site" (as predicted by Applicant) and forms part of Applicant's rationale for the present invention—said rationale does not constitute an essential technical feature of the present invention.

"Sequence identity" between amino acid or nucleic acid sequences can be determined by comparing a position in each of the sequences which may be aligned for the purposes of comparison. When a position in the compared sequences is occupied by the same nucleotide or amino acid, then the sequences are identical at that position. A degree of identity between amino acid sequences is a function of the number of identical amino acid sequences that are shared between these sequences. A degree of sequence identity between nucleic acids is a function of the number of identical nucleotides at positions shared by these sequences.

To determine the "percentage of sequence identity" between two amino acid sequences or two nucleic acid sequences, the sequences are aligned for optimal comparison. For example, gaps can be introduced in the sequence of a first amino acid sequence or a first nucleic acid sequence for optimal alignment with the second amino acid sequence or second nucleic acid sequence. The amino acid residues or nucleotides at corresponding amino acid positions or nucleotide positions are then compared. When a position in the first sequence is occupied by the same amino acid residue or nucleotide as the corresponding position in the second sequence, the molecules are identical at that position.

The percentage (%) of identity between the two sequences is a function of the number of identical positions shared by the sequences. Hence, the percentage of identity can be calculated by multiplying the number of identical positions by 100 and dividing by the length of the aligned region (overlapping positions), including gaps (only internal gaps, not the gaps at the sequence ends).

In this comparison, the sequences can be of the same length, or may be of different lengths. Identity scoring only counts perfect matches, and does not consider the degree of similarity of amino acids to one another.

Optimal alignment of sequences may be herein preferably conducted by a global homology alignment algorithm should the alignment be performed using sequences of the same or similar length, such as by the algorithm described by Needleman and Wunsch (Journal of Molecular Biology; 1970, 48 (3): 443-53), by computerized implementations of this algorithm (e.g., using the DNASTAR® Lasergene software), or by visual inspection. Alternatively, should the alignment be performed using sequences of distinct length (e.g. the amino acid sequence of the light-chain according to the invention versus the entire amino acid sequence of a naturally-occuring botulinum neurotoxin), the optimal alignment of sequences can be herein preferably conducted by a local homology alignment algorithm, such as by the algorithm described by Smith and Waterson (Journal of Molecular Biology; 1981, 147: 195-197), by computerized implementations of this algorithm (e.g., using the DNASTAR® Lasergene software), or by visual inspection. The best alignment (i.e., resulting in the highest percentage of identity between the compared sequences) generated by the various methods is selected. Examples of global and local homology alignment algorithms are well-known to the skilled practitioner, and include, without limitation, ClustalV (global alignment), ClustalW (local alignment) and BLAST (local alignment).

The skilled practitioner would further readily understand that the present invention embraces modified BoNT/A L-chains that are substantially homologous, and which retain the capacity to cleave hSNAP-23, i.e. functional variants or homologs. These functional variants or homologs can be characterized as having one or more amino acid mutations (such as an amino acid deletion, addition, and/or substitution) other than the ones disclosed thereafter with regard to hSNAP-23 cleavage, and which do not significantly affect the folding or protease activity, in particular hSNAP-23 cleavage. For example, such mutations include, without limitation, conservative substitutions, small deletions (typically of 1 to about 30 amino acids), small amino- or carboxyl-terminal extensions (such as an amino-terminal methionine residue), addition of a small linker peptide of up to about 20-25 residues or of an affinity tag.

Functional variants or homologs according to the invention preferably comprise mutations of minor nature, such as conservative amino acid substitions. Conservative amino acid substitutions are well-known to the skilled practitioner, and include, without limitation:

Basic: arginine, lysine, histidine
Acidic: glutamic acid, aspartic acid
Polar: glutamine, asparagine
Hydrophobic: leucine, isoleucine, valine, methionine
Aromatic: phenylalanine, tryptophan, tyrosine
Small: glycine, alanine, serine, threonine In addition to the 20 standard amino acids, non-standard amino acids (such as 4-hydroxyproline, 6-N-methyl lysine, 2-aminoisobutyric acid, isovaline and a-methyl serine) may be substituted for amino acid residues of the polypeptides, of the present invention. A limited number of non-conservative amino acids, amino acids that are not encoded by the genetic code, and unnatural amino acids may be substituted for clostridial polypeptide amino acid residues. The polypeptides of the present invention may also comprise non-naturally occurring amino acid residues.

Non-naturally occurring amino acids include, without limitation, trans-3-methylproline, 2,4-methano-proline, cis-4-hydroxyproline, trans-4-hydroxyproline, N-methylglycine, allo-threonine, methyl-threonine, hydroxyethylcysteine, hydroxyethylhomo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine. Several methods are known in the art for incorporating non-naturally occurring amino acid residues into proteins.

The amino acid substitution may comprise the substitution of an amino acid comprising a certain physiochemical property (e.g. hydrophobicity) with an amino acid having a similar or alternative property. Examples of such subsitutions are Misted below:

Acidic amino acid substituted for a neutral, polar amino acid;
Polar amino acid substituted for a non-polar amino acid;
Non-polar amino acid substituted for a non-polar amino acid;
Non-polar amino acid substituted for a polar amino acid;
Polar amino acid substituted for a basic amino acid;
Non-polar amino acid substituted for an acidic amino acid;
Non-polar amino acid substituted for a polar amino acid.

Accordingly, the L-chain of all BoNT/A subtypes, such as any of BoNT/A1 to BoNT/A8 L-chain, which comprise one or more of the mutations as described herein for cleavage of hSNAP-23, are encompassed by the present invention. Said BoNT/A L-chain may additionally comprise further mutations to provide a non-native activation cleavage site, such as the cleavage site of enterokinase (SEQ ID NO: 10), PreScission, Factor Xa, Thrombin, TEV protease, etc.

Additional definitions are provided throughout the specification.

The present invention can be described as follows.

In a first aspect, the present invention provides a modified botulinum neurotoxin A (BoNT/A) L-chain protease that cleaves human SNAP-23 (hSNAP-23), having a modified amino acid sequence relative to the wild-type BoNT/A L-chain (SEQ ID NO: 1), that comprises:
  a) at least one amino acid residue change located within a first BoNT/A L-chain protease binding pocket for binding to the P182/D178 binding site of hSNAP-23;
  b) wherein said first BoNT/AL-chain protease binding pocket is defined by amino acid residues E148, T307, A308 and Y312 of wild-type BoNT/A L-chain (SEQ ID NO: 1);
  c) and wherein said at least one amino acid residue change comprises:
    i. an amino acid residue selected from the group consisting of asparagine and tyrosine at the position on the modified L-chain protease amino acid sequence that corresponds to amino acid residue E148 of wild-type BoNT/A L-chain (SEQ ID NO: 1); and/ or
    ii. an amino acid residue selected from the group consisting of phenylalanine, isoleucine and leucine at the position on the modified L-chain protease amino acid sequence that corresponds to amino acid residue T307 of wild-type BoNT/A L-chain (SEQ ID NO: 1); and/ or
    iii. an amino acid residue selected from the group consisting of proline, asparagine, threonine and isoleucine at the position on the modified L-chain protease amino acid sequence that corresponds to amino acid residue A308 of wild-type BoNT/A L-chain (SEQ ID NO: 1); and/ or
    iv. an amino acid residue selected from the group consisting of lysine, valine, methionine and leucine at the position on the modified L-chain protease amino acid sequence that corresponds to amino acid residue Y312 of wild-type BoNT/A L-chain (SEQ ID NO: 1).

Without wishing to be bound by any theory, Applicant believes that the above-defined BoNT/A L-chain binding pocket effects an important enzyme-substrate association with the recognition sequence on hSNAP-23.

Thus, the present invention is predicated on the surprising finding (e.g. unexpected technical effect) that targeted amino acid substitutions as claimed allow for the generation of BoNT/A L-chain(s) increased hSNAP-23 cleavage (relative to wild-type BoNT/A L-chain). The present inventors have not only successfully indentified suitable amino acid positions of BoNT/A L-chain which can be altered (e.g. substituted) to increase hSNAP-23 cleavage, but have also identified precise amino acid substitutions which provide this effect.

In a first aspect, the present invention provides a modified botulinum neurotoxin A (BoNT/A) L-chain protease that cleaves human SNAP-23 (hSNAP-23), having a modified amino acid sequence relative to the wild-type BoNT/A L-chain (SEQ ID NO: 1), that comprises:
  a) at least one amino acid residue change located within a first BoNT/A L-chain protease binding pocket for binding to the P182/D178 binding site of hSNAP-23;
  b) wherein said first BoNT/AL-chain protease binding pocket is defined by amino acid residue E148 of wild-type BoNT/A L-chain (SEQ ID NO: 1);
  c) and wherein said at least one amino acid residue change comprises:
    i. an amino acid residue selected from the group consisting of asparagine and tyrosine at the position on the modified L-chain protease amino acid sequence that corresponds to amino acid residue E148 of wild-type BoNT/A L-chain (SEQ ID NO: 1).

In one aspect, the present invention provides a modified botulinum neurotoxin A (BoNT/A) L-chain protease that cleaves human SNAP-23 (hSNAP-23), having a modified amino acid sequence relative to the wild-type BoNT/A L-chain (SEQ ID NO: 1), that comprises:
  a) at least one amino acid residue change located within a first BoNT/A L-chain protease binding pocket for binding to the P182/D178 binding site of hSNAP-23;
  b) wherein said first BoNT/AL-chain protease binding pocket is defined by amino acid residues E148, T307, A308 and Y312 of wild-type BoNT/A L-chain (SEQ ID NO: 1);
  c) and wherein said at least one amino acid residue change comprises:
    i. an amino acid residue selected from the group consisting of phenylalanine, isoleucine and leucine at the position on the modified L-chain protease amino acid sequence that corresponds to amino acid residue T307 of wild-type BoNT/A L-chain (SEQ ID NO: 1); and/ or
    ii. an amino acid residue selected from the group consisting of proline, asparagine, threonine and isoleucine at the position on the modified L-chain protease amino acid sequence that corresponds to amino acid residue A308 of wild-type BoNT/A L-chain (SEQ ID NO: 1); and/ or
    iii. an amino acid residue selected from the group consisting of lysine, valine, methionine and leucine at the position on the modified L-chain protease amino acid sequence that corresponds to amino acid residue Y312 of wild-type BoNT/A L-chain (SEQ ID NO: 1).

A modified BoNT/A L-chain may comprise one amino acid subsitution (relative to wildtype SEQ ID NO:1). A modified BoNT/A L-chain may comprise two amino acid subsitutions (relative wildtype WT SEQ ID NO:1). A modified BoNT/A L-chain may comprise three amino acid subsitutions (relative to wildtype SEQ ID NO:1). A modified BoNT/A L-chain may comprise four amino acid subsitutions (relative to wildtype SEQ ID NO:1).

Modified BoNT/A L-chains of the present invention comprising a binding pocket mutation for the P182/D178 binding site on hSNAP-23 typically demonstrate at least a 1.15-fold increased hSNAP-23 cleavage (versus wild-type BoNT/A L-chain)—see the $1^{st}$ data column in FIG. 1A. Examples of such modified BoNT/A L-chains (referred to by the amino acid substitution(s) relative to a corresponding wild-type BoNT/A L-chain SEQ ID NO:1) include:

a modified BoNT/A L-chain comprising the substitution E148Y or E148N;

a modified BoNT/A L-chain comprising the substitution T307I, A308P, and Y312V;

a modified BoNT/A L-chain comprising the substitution T307F, A308N, and Y312L;

a modified BoNT/A L-chain comprising the substitution E148N, T307I, and A308P, Y312V;

a modified BoNT/A L-chain comprising the substitution E148Y, T307F, A308N, and Y312L;

a modified BoNT/A L-chain comprising the substitution E148Y, T307I, A308P, and Y312V;

a modified BoNT/A L-chain comprising the substitution E148Y, T307L, A308T, and Y312M;

a modified BoNT/A L-chain comprising the substitution E148Y, T307L, A308I, and Y312M.

In one embodiment, modified BoNT/A L-chains of the present invention comprising a binding pocket mutation for the P182/D178 binding site on hSNAP-23 demonstrate at least a 1.35-fold increased hSNAP-23 cleavage (versus wild-type BoNT/A L-chain)—see the $1^{st}$ data column in FIG. 1A. Examples of such modified BoNT/A L-chains (referred to by the amino acid substitution(s) relative to a corresponding wild-type BoNT/A L-chain SEQ ID NO:1) include:

a modified BoNT/A L-chain comprising the substitution E148Y or E148N;

a modified BoNT/A L-chain comprising the substitution T307I, A308P, and Y312V;

a modified BoNT/A L-chain comprising the substitution T307F, A308N, and Y312L;

a modified BoNT/A L-chain comprising the substitution E148N, T307I, A308P, and Y312V;

a modified BoNT/A L-chain comprising the substitution E148Y, T307F, A308N, and Y312L;

a modified BoNT/A L-chain comprising the substitution E148Y, T307I, A308P, and Y312V;

a modified BoNT/A L-chain comprising the substitution E148Y, T307L, A308T, and Y312M;

a modified BoNT/A L-chain comprising the substitution E148Y, T307L, A308I, and Y312M.

In another embodiment, modified BoNT/A L-chains of the present invention comprising a binding pocket mutation for the P182/D178 binding site on hSNAP-23 demonstrate at least a 1.7-fold increased hSNAP-23 cleavage (versus wild-type BoNT/A L-chain)—see the $1^{st}$ data column in FIG. 1A. Examples of such modified BoNT/A L-chains (referred to by the amino acid substitution(s) relative to a corresponding wild-type BoNT/A L-chain SEQ ID NO:1) include:

a modified BoNT/A L-chain comprising the substitution E148Y;

a modified BoNT/A L-chain comprising the substitution T307F;

a modified BoNT/A L-chain comprising the substitution T307I;

a modified BoNT/A L-chain comprising the substitution Y312K;

a modified BoNT/A L-chain comprising the substitution Y312K, E148Y;

a modified BoNT/A L-chain comprising the substitution T307I, A308P, and Y312V;

a modified BoNT/A L-chain comprising the substitution E148N, T307I, A308P, and Y312V;

a modified BoNT/A L-chain comprising the substitution E148Y, T307F, A308N, and Y312L;

a modified BoNT/A L-chain comprising the substitution E148Y, T307L, A308T, and Y312M.

In a further embodiment, modified BoNT/A L-chains of the present invention comprising a binding pocket mutation for the P182/D178 binding site on hSNAP-23 may demonstrate at least a 2.0-fold increased hSNAP-23 cleavage (versus wild-type BoNT/A L-chain)—see the $1^{st}$ data column in FIG. 1A. Examples of such modified BoNT/A L-chains (referred to by the amino acid substitution(s) relative to a corresponding wild-type BoNT/A L-chain SEQ ID NO:1) include:

a modified BoNT/A L-chain comprising the substitution E148Y;

a modified BoNT/A L-chain comprising the substitution E148N, T307I, A308P, and Y312V;

a modified BoNT/A L-chain comprising the substitution E148Y, T307F, A308N, and Y312L;

a modified BoNT/A L-chain comprising the substitution E148Y, T307L, A308T, and Y312M.

In a further embodiment, modified BoNT/A L-chains of the present invention comprising a binding pocket mutation for the P182/D178 binding site on hSNAP-23 may demonstrate at least a 4.0-fold increased hSNAP-23 cleavage (versus wild-type BoNT/A L-chain)—see the $1^{st}$ data column in FIG. 1A. Examples of such modified BoNT/A L-chains (referred to by the amino acid substitution(s) relative to a corresponding wild-type BoNT/A L-chain SEQ ID NO:1) include:

a modified BoNT/A L-chain comprising the substitution E148Y;

a modified BoNT/A L-chain comprising the substitution E148N, T307I, A308P, and Y312V;

a modified BoNT/A L-chain comprising the substitution E148Y, T307F, A308N, and Y312L;

a modified BoNT/A L-chain comprising the substitution E148Y, T307L, A308T, and Y312M.

In another embodiment, modified BoNT/A L-chains of the present invention comprising a binding pocket mutation for the P182/D178 binding site on hSNAP23 demonstrate at least a 6.0-fold, preferably at least a 7.0-fold, more preferably at least a 8.0-fold increased hSNAP-23 cleavage (versus wild-type BoNT/A L-chain)—see the $1^{st}$ data column in FIG. 1A. Examples of such modified BoNT/A L-chains (referred to by the amino acid substitution(s) relative to a corresponding wild-type BoNT/A L-chain SEQ ID NO:1) include: a modified BoNT/A L-chain comprising the substitution E148Y.

Modified BoNT/A L-chains of the present invention comprising a binding pocket mutation for the P182/D178 binding site on hSNAP-23 typically demonstrate greater than 1.5% hSNAP-23 cleavage (% at 1 micromolar modified BoNT/A L-chain; 20 micromolar hSNAP-23; preferably incubated at about 37° C. for about 1 hour)—see the $2^{nd}$ data column in FIG. 1A. For reference, wild-type BoNT/A L-chain (e.g. SEQ ID NO: 1) demonstrates less than 0.5% hSNAP-23 cleavage (% at 1 micromolar modified BoNT/A L-chain; 20 micromolar hSNAP-23; preferably incubated at about 37° C. for about 1 hour). Examples of such modified L-chains (referred to by the amino acid substitution(s) relative to a corresponding wild-type BoNT/A L-chain SEQ ID NO:1) include:

a modified BoNT/A L-chain comprising the substitution E148Y;

a modified BoNT/A L-chain comprising the substitution T307F;

a modified BoNT/A L-chain comprising the substitution T307I;

a modified BoNT/A L-chain comprising the substitution Y312K;

a modified BoNT/A L-chain comprising the substitution Y312K, and E148Y.

In one embodiment, modified BoNT/A L-chains of the present invention comprising a binding pocket mutation for the P182/D178 binding site on hSNAP-23 typically demonstrate greater than 2% hSNAP-23 cleavage (% at 1 micromolar modified BoNT/A L-chain; 20 micromolar hSNAP-23; preferably incubated at about 37° C. for about 1 hour)—see the $2^{nd}$ data column in FIG. 1A. Examples of such modified L-chains (referred to by the amino acid substitution(s) relative to a corresponding wild-type BoNT/A L-chain SEQ ID NO:1) include:

a modified BoNT/A L-chain comprising the substitution E148Y;

a modified BoNT/A L-chain comprising the substitution T307I;

a modified BoNT/A L-chain comprising the substitution Y312K.

In a further embodiment, modified BoNT/A L-chains of the present invention comprising a binding pocket mutation for the P182/D178 binding site on hSNAP-23 demonstrate at least 9% increased hSNAP-23 cleavage (% at 1 micromolar modified BoNT/A L-chain; 20 micromolar hSNAP-23; preferably incubated at about 37° C. for about 1 hour)—see the $2^{nd}$ data column in FIG. 1A. Examples of such modified BoNT/A L-chains (referred to by the amino acid substitution(s) relative to a corresponding wild-type BoNT/A L-chain SEQ ID NO:1) include:

a modified BoNT/A L-chain comprising the substitution E148Y.

Additional examples of modified BoNT/A L-chain mutants having a binding pocket mutation for the P182/D178 binding site on hSNAP-23 (referred to by the amino acid substitution(s) relative to a corresponding wild-type BoNT/A L-chain SEQ ID NO:1) include:

a modified BoNT/A L-chain comprising the substitution A308L;

a modified BoNT/A L-chain comprising the substitution A308V;

a modified BoNT/A L-chain comprising the substitution A308I;

a modified BoNT/A L-chain comprising the substitution A308P;

a modified BoNT/A L-chain comprising the substitution A308N;

a modified BoNT/A L-chain comprising the substitution A308T;

a modified BoNT/A L-chain comprising the substitution Y312V;

a modified BoNT/A L-chain comprising the substitution Y312M;

a modified BoNT/A L-chain comprising the substitution Y312L.

A modified BoNT/A L-chain of the present invention having a binding pocket mutation for the P182/D178 binding site on hSNAP-23 can comprise one or more amino acid residue changes relative to the wild-type BoNT/A L-chain, as herein before defined. By way of illustration, a modified BoNT/A L-chain of the present invention may have a single amino acid residue mutation (within the binding pocket for the P182/D178 binding site on hSNAP-23, as defined above), for example a mutation corresponding to amino acid residue E148 of wild-type BoNT/A L-chain (SEQ ID NO: 1). Similarly, a modified BoNT/A L-chain of the present invention may comprise more than one amino acid residue mutation (within the binding pocket for the P182/D178 binding site on hSNAP-23, as defined above), for example mutations corresponding to amino acid residues T307, A308 and Y312 of wild-type BoNT/A L-chain (SEQ ID NO: 1).

In a preferred embodiment, a modified BoNT/A L-chain of the present invention having one or more binding pocket mutations for the P182/D178 binding site on hSNAP-23 further comprises one or more mutations within one or more different BoNT/A L-chain binding pockets for hSNAP-23 as further described below.

Said one or more different BoNT/A L-chain binding pockets for hSNAP-23 include a second BoNT/A L-chain protease binding pocket for binding to the D189/D192 binding site of hSNAP-23; a third BoNT/A L-chain protease binding pocket for binding to the 1198 binding site of hSNAP-23; a fourth BoNT/A L-chain protease binding pocket for binding to the K185 binding site of hSNAP-23; a fifth BoNT/A L-chain protease binding pocket for binding to the R186 binding site of hSNAP-23; a sixth BoNT/A L-chain protease binding pocket for binding to the K206 binding site of hSNAP-23; a seventh BoNT/A L-chain protease binding pocket for binding to the D210 binding site of hSNAP-23; an eighth BoNT/A L-chain protease binding pocket for binding to the D168 binding site of hSNAP-23.

Alternatively, according to distinct technical features of the invention, a modified BoNT/A L-chain can comprise one or more mutations within one or more BoNT/A L-chain binding pockets other than within the binding pocket for the P182/D178 binding site on hSNAP23 as defined above.

Said BoNT/A L-chain binding pockets for hSNAP-23 and corresponding mutations of interest are further detailed hereunder.

Accordingly, as an additional technical feature, or as an alternative technical feature), the present invention includes BoNT/A L-chain mutants comprising one or more mutations within a herein defined pocket of the BoNT/A L-chain. By way of example, a modified BoNT/A L-chain of the present invention that cleaves human SNAP-23 (hSNAP-23) has a modified amino acid sequence relative to the wild-type BoNT/A L-chain (SEQ ID NO: 1) that comprises:

a) an amino acid residue change located within a fifth BoNT/A L-chain protease binding pocket for binding to the R186 binding site of hSNAP-23;

b) wherein said fifth BoNT/A L-chain protease binding pocket is defined by amino acid residue S143 of wild-type BoNT/A L-chain (SEQ ID NO: 1);

c) and wherein said amino acid residue change comprises:
  i. an amino acid residue selected from the group consisting of glutamine, glutamate and aspartate at the position on the modified L-chain protease amino acid sequence that corresponds to amino acid residue S143 of wild-type BoNT/A L-chain (SEQ ID NO: 1).

Without wishing to be bound by any theory, Applicant believes that the above-defined BoNT/A L-chain binding pocket provides a stabilising salt bridge between R186 on hSNAP-23 and S143 on BoNT/A.

Modified BoNT/A L-chains of the present invention comprising a binding pocket mutation for the R186 binding site on hSNAP-23 typically demonstrate a $K_M$ for hSNAP-23 of less than 100 micromolar, for example less than 95 micromolar—see the $3^{rd}$ data column in FIG. 1A. For reference, wild-type BoNT/A L-chain (e.g. SEQ ID NO: 1) demonstrates a $K_M$ for hSNAP-23 that is greater than 150 micromolar, for example greater than 200 micromolar. Examples of such modified BoNT/A L-chains (referred to by the amino acid substitution(s) relative to a corresponding wild-type BoNT/A L-chain SEQ ID NO:1) include:

a modified BoNT/A L-chain comprising the substitution V304D;

a modified BoNT/A L-chain comprising the substitution V304E;

a modified BoNT/A L-chain comprising the substitution G305D;

a modified BoNT/A L-chain comprising the substitution G305E;

a modified BoNT/A L-chain comprising the substitution S143D;

a modified BoNT/A L-chain comprising the substitution S143E;

a modified BoNT/A L-chain comprising the substitution S143Q;

a modified BoNT/A L-chain comprising the substitution K166F.

In a preferred embodiment, a modified BoNT/A L-chain of the present invention having a binding pocket mutation for the R186 binding site on hSNAP-23 can further comprise one or more mutations within one or more different BoNT/A L-chain binding pockets as herein described (e.g. within the binding pocket for the P182/D178 binding site on hSNAP-23, as defined above). Such mutants typically demonstrate at least a 0.5-fold decreased hSNAP-23 cleavage (versus E148Y modified BoNT/A L-chain), or, in other words at least a 4.0-fold increased hSNAP-23 cleavage (versus wild-type BoNT/A L-chain)—see the $1^{st}$ data column for multi-pocket mutants in FIG. 1B; or at least 5% hSNAP-23 cleavage (% at 1 micromolar modified BoNT/A L-chain; 20 micromolar hSNAP-23; preferably incubated at about 37° C. for about 1 hour)—see the $2^{nd}$ data column in FIG. 1B. Examples of such modified BoNT/A L-chains (referred to by the amino acid substitution(s) relative to a corresponding wild-type BoNT/A L-chain SEQ ID NO:1) include:

a modified BoNT/A L-chain comprising the substitution E148Y, and S143E;

a modified BoNT/A L-chain comprising the substitution E148Y, and S143D;

a modified BoNT/A L-chain comprising the substitution E148Y, and S143Q.

Thus, in one embodiment there is provided a modified BoNT/A L-chain protease that cleaves human SNAP-23 (hSNAP-23), and having a modified amino acid sequence relative to the wild-type BoNT/A L-chain (SEQ ID NO: 1) that comprises:

a) an amino acid residue change located within a first BoNT/A L-chain protease binding pocket for binding to the P182/D178 binding site of hSNAP-23; wherein said first BoNT/A L-chain protease binding pocket is defined by amino acid residue E148 of wild-type BoNT/A L-chain (SEQ ID NO: 1); and b) an amino acid residue change located within a fifth BoNT/A L-chain protease binding pocket for binding to the R186 binding site of hSNAP-23; wherein said fifth BoNT/A L-chain protease binding pocket is defined by amino acid residue S143 of wild-type BoNT/A L-chain (SEQ ID NO: 1); and c) and wherein said amino acid residue change comprises:
i. an amino acid residue selected from the group consisting of tyrosine at the position on the modified L-chain protease amino acid sequence that corresponds to amino acid residue E148 of wild-type BoNT/A L-chain (SEQ ID NO: 1); and ii. an amino acid residue selected from the group consisting of glutamate at the position on the modified L-chain protease amino acid sequence that corresponds to amino acid residue S143 of wild-type BoNT/A L-chain (SEQ ID NO: 1).

In another embodiment there is provided a modified BoNT/A L-chain protease that cleaves human SNAP-23 (hSNAP-23), and having a modified amino acid sequence relative to the wild-type BoNT/A L-chain (SEQ ID NO: 1) that comprises:

a) an amino acid residue change located within a first BoNT/A L-chain protease binding pocket for binding to the P182/D178 binding site of hSNAP-23; wherein said first BoNT/A L-chain protease binding pocket is defined by amino acid residue E148 of wild-type BoNT/A L-chain (SEQ ID NO: 1); and b) an amino acid residue change located within a fifth BoNT/A L-chain protease binding pocket for binding to the R186 binding site of hSNAP-23; wherein said fifth BoNT/A L-chain protease binding pocket is defined by amino acid residue S143 of wild-type BoNT/A L-chain (SEQ ID NO: 1);

c) and wherein said amino acid residue change comprises:
i. an amino acid residue selected from the group consisting of tyrosine at the position on the modified L-chain protease amino acid sequence that corresponds to amino acid residue E148 of wild-type BoNT/A L-chain (SEQ ID NO: 1); and ii. an amino acid residue selected from the group consisting of aspartate at the position on the modified L-chain protease amino acid sequence that corresponds to amino acid residue S143 of wild-type BoNT/A L-chain (SEQ ID NO: 1).

In another embodiment, a modified BoNT L-chain of the present invention having a binding pocket mutation for the R186 binding site on hSNAP-23 further comprises one or more mutations within one or more different BoNT/A L-chain binding pockets as herein described (e.g. within the binding pocket for the P182/D178 binding site on hSNAP-23, as defined above). Such mutants typically demonstrate at least a 2.0-fold increased hSNAP-23 cleavage (versus E148Y modified BoNT/A L-chain)—see the $1^{st}$ data column for multi-pocket mutants in FIG. 1B. Examples of such modified BoNT/A L-chains (referred to by the amino acid substitution(s) relative to a corresponding wild-type BoNT/A L-chain SEQ ID NO:1) include:

a modified BoNT/A L-chain having the substitution E148Y, and S143E;

a modified BoNT/A L-chain having the substitution E148Y, and S143D.

In another embodiment, a modified BoNT L-chain of the present invention having a binding pocket mutation for the R186 binding site on hSNAP-23 further comprises one or more mutations within one or more different BoNT/A L-chain binding pockets as herein described (e.g. within the binding pocket for the P182/D178 binding site on hSNAP-23, as defined above). Such mutants typically demonstrate at least a 3.0-fold increased hSNAP-23 cleavage (as a percentage versus E148Y modified BoNT/A L-chain)—see the $1^{st}$ data column for multi-pocket mutants in FIG. 1B. Examples of such modified BoNT/A L-chains (referred to by the amino acid substitution(s) relative to a corresponding wild-type BoNT/A L-chain SEQ ID NO:1) include:

a modified BoNT/A L-chain comprising the substitution E148Y, S143D.

As an additional technical feature, or as an alternative technical feature, the present invention includes BoNT/A L-chain mutants comprising one or more mutations within a herein defined pocket of the BoNT/A L-chain. By way of example, a modified BoNT/A L-chain of the present invention that cleaves human SNAP-23 (hSNAP-23) has a modified amino acid sequence relative to the wild-type BoNT/A L-chain (SEQ ID NO: 1), that comprises:

a) at least one amino acid residue change located within a fourth BoNT/A L-chain protease binding pocket for binding to the K185 binding site of hSNAP-23;

b) wherein said fourth BoNT/A L-chain protease binding pocket is defined by amino acid residues V304 and G305 of wild-type BoNT/A L-chain (SEQ ID NO: 1);

c) and wherein said at least one amino acid residue change comprises:

i. an amino acid residue selected from the group consisting of glutamate and aspartate at the position on the modified L-chain protease amino acid sequence that corresponds to amino acid residue V304 of wild-type BoNT/A L-chain (SEQ ID NO: 1); and/or ii. an amino acid residue selected from the group consisting of glutamate and aspartate at the position on the modified L-chain protease amino acid sequence that corresponds to amino acid residue G305 of wild-type BoNT/A L-chain (SEQ ID NO: 1).

Without wishing to be bound by any theory, Applicant believes that the above-defined BoNT/A L-chain binding pocket provides a stabilising salt bridge between K185 on hSNAP-23 and BoNT/A.

Modified BoNT/A L-chains of the present invention comprising a binding pocket mutation for the K185 binding site on hSNAP-23 typically demonstrate a $K_M$ for hSNAP-23 of less than 100 micromolar—see the $3^{rd}$ data column in FIG. 1A. For reference, wild-type BoNT/A L-chain (e.g. SEQ ID NO: 1) demonstrates a $K_M$ for hSNAP-23 that is greater than 150 micromolar, for example greater than 200 micromolar. Examples of such modified BoNT/A L-chains (referred to by the amino acid substitution(s) relative to a corresponding wild-type BoNT/A L-chain SEQ ID NO:1) include:

a modified BoNT/A L-chain comprising the substitution V304D;

a modified BoNT/A L-chain comprising the substitution V304E;

a modified BoNT/A L-chain comprising the substitution G305D;

a modified BoNT/A L-chain comprising the substitution G305E.

A modified BoNT/A L-chain of the present invention having a binding pocket mutation for the K185 binding site on hSNAP-23 comprises one or more amino acid residue changes relative to the wild-type BoNT/A L-chain, as herein before defined. By way of illustration, a modified BoNT/A L-chain of the present invention may have a single amino acid residue mutation (within the binding pocket for the K185 binding site on hSNAP-23, as defined above), for example a mutant corresponding to amino acid residue G305 of wild-type BoNT/A L-chain (SEQ ID NO: 1). Similarly, a modified BoNT/A L-chain of the present invention may comprise more than one mutation (within the binding pocket for the K185 binding site on hSNAP-23 as defined above), for example corresponding to amino acid residues V304 and G305 of wild-type BoNT/A L-chain (SEQ ID NO: 1).

In a preferred embodiment, a modified BoNT/A L-chain of the present invention having a binding pocket mutation for the K185 binding site on hSNAP-23 can further comprise one or more mutations within one or more different BoNT/A L-chain binding pockets for hSNAP-23 as herein described (e.g. within the binding pocket for the P182/D178 binding site on hSNAP-23, as defined above). Such mutants typically demonstrate at least a 2.0-fold, preferably at least a 2.5-fold increased hSNAP-23 cleavage (versus E148Y modified BoNT/A L-chain)—see the $1^{st}$ data column for multi-pocket mutants in FIG. 1B. Examples of such modified BoNT/A L-chains (referred to by the amino acid substitution(s) relative to a corresponding wild-type BoNT/A L-chain SEQ ID NO:1) include:

a modified BoNT/A L-chain having the substitution E148Y, and G305D.

Thus, in another embodiment there is provided a modified BoNT/A L-chain protease that cleaves human SNAP-23 (hSNAP-23), and having a modified amino acid sequence relative to the wild-type BoNT/A L-chain (SEQ ID NO: 1) that comprises:

a) an amino acid residue change located within a first BoNT/A L-chain protease binding pocket for binding to the P182/D178 binding site of hSNAP-23; wherein said first BoNT/A L-chain protease binding pocket is defined by amino acid residue E148 of wild-type BoNT/A L-chain (SEQ ID NO: 1); and b) an amino acid residue change located within a fourth BoNT/A L-chain protease binding pocket for binding to the K185 binding site of hSNAP-23; wherein said fourth BoNT/A L-chain protease binding pocket is defined by amino acid residue G305 of wild-type BoNT/A L-chain (SEQ ID NO: 1);

c) and wherein said amino acid residue change comprises:

i. an amino acid residue selected from the group consisting of tyrosine at the position on the modified L-chain protease amino acid sequence that corresponds to amino acid residue E148 of wild-type BoNT/A L-chain (SEQ ID NO: 1); and ii. an amino acid residue selected from the group consisting of aspartate at the position on the modified L-chain protease amino acid sequence that corresponds to amino acid residue G305 of wild-type BoNT/A L-chain (SEQ ID NO: 1).

Still, as an additional technical feature, or as an alternative technical feature, the present invention includes BoNT/A L-chain mutants comprising one or more mutations within a herein defined pocket of the BoNT/A L-chain. By way of example, a modified BoNT/A L-chain of the present invention that cleaves human SNAP-23 (hSNAP-23) has a modified amino acid sequence relative to the wild-type BoNT/A L-chain (SEQ ID NO: 1), that comprises:

a) an amino acid residue change located within a second BoNT/A L-chain protease binding pocket for binding to the D189/D192 binding site of hSNAP-23;

b) wherein said second BoNT/A L-chain protease binding pocket is defined by amino acid residue Q29 of wild-type BoNT/A L-chain (SEQ ID NO: 1);

c) and wherein said amino acid residue change comprises:

i. an amino acid residue alanine at the position on the modified L-chain protease amino acid sequence that corresponds to amino acid residue Q29 of wild-type BoNT/A L-chain (SEQ ID NO: 1).

Without wishing to be bound by any theory, Applicant believes that the above-defined BoNT/A L-chain binding pocket provides a stabilising interaction between D189/D192 on hSNAP-23 and amino acid 29 of BoNT/A or close-by amino acids.

Examples of such modified BoNT/A L-chains (referred to by the amino acid substitution(s) relative to a corresponding wild-type BoNT/A L-chain SEQ ID NO:1) include:

a modified BoNT/A L-chain having the substitution Q29A.

In a preferred embodiment, a modified BoNT L-chain of the present invention having a binding pocket mutation for the D189/D192 binding site on hSNAP-23 further comprises one or more mutations within one or more different BoNT/A L-chain binding pockets as herein described (e.g. within the binding pocket for the P182/D178 binding site on hSNAP-23, as defined above). Such mutants typically demonstrate at least a 1.50-fold % increased hSNAP-23 cleavage (versus E148Y modified BoNT/A L-chain)—see the 1$^{st}$ data column presented for multi-pocket mutants in FIG. 1B. Examples of such modified BoNT/A L-chains (referred to by the amino acid substitution(s) relative to a corresponding wild-type BoNT/A L-chain SEQ ID NO:1) include:

a modified BoNT/A L-chain having the substitution E148Y, Q29A.

Thus, in another embodiment there is provided a modified BoNT/A L-chain protease that cleaves human SNAP-23 (hSNAP-23), and having a modified amino acid sequence relative to the wild-type BoNT/A L-chain (SEQ ID NO: 1) that comprises:
- a) an amino acid residue change located within a first BoNT/A L-chain protease binding pocket for binding to the P182/D178 binding site of hSNAP-23; wherein said first BoNT/A L-chain protease binding pocket is defined by amino acid residue E148 of wild-type BoNT/A L-chain (SEQ ID NO: 1); and
- b) an amino acid residue change located within a second BoNT/A L-chain protease binding pocket for binding to the D189/D192 binding site of hSNAP-23; wherein said second BoNT/A L-chain protease binding pocket is defined by amino acid residue Q29 of wild-type BoNT/A L-chain (SEQ ID NO: 1);
- c) and wherein said amino acid residue change comprises:
  - i. an amino acid residue selected from the group consisting of tyrosine at the position on the modified L-chain protease amino acid sequence that corresponds to amino acid residue E148 of wild-type BoNT/A L-chain (SEQ ID NO: 1); and
  - ii. an amino acid residue selected from the group consisting of alanine at the position on the modified L-chain protease amino acid sequence that corresponds to amino acid residue Q29 of wild-type BoNT/A L-chain (SEQ ID NO: 1).

In another embodiment, a modified BoNT L-chain of the present invention having a binding pocket mutation for the D189/D192 binding site on hSNAP-23 can further comprise one or more mutations within at least two different BoNT/A L-chain binding pockets as herein described (e.g. within the binding pocket for the P182/D178 binding site on hSNAP-23, and within the binding pocket for the R186 binding site on hSNAP-23, both as defined above). Such mutants typically demonstrate at least a 2.5-fold increased hSNAP-23 cleavage (versus E148Y modified BoNT/A L-chain—see the 1$^{st}$ data column presented in FIG. 1B. Examples of such modified BoNT/A L-chains (referred to by the amino acid substitution(s) relative to a corresponding wild-type BoNT/A L-chain SEQ ID NO:1) include:

a modified BoNT/A L-chain comprising the substitution E148Y, Q29A, and S143D.

Thus, in another embodiment there is provided a modified BoNT/A L-chain protease that cleaves human SNAP-23 (hSNAP-23), and having a modified amino acid sequence relative to the wild-type BoNT/A L-chain (SEQ ID NO: 1) that comprises:
- a) an amino acid residue change located within a first BoNT/A L-chain protease binding pocket for binding to the P182/D178 binding site of hSNAP-23; wherein said first BoNT/A L-chain protease binding pocket is defined by amino acid residue E148 of wild-type BoNT/A L-chain (SEQ ID NO: 1); and
- b) an amino acid residue change located within a second BoNT/A L-chain protease binding pocket for binding to the D189/D192 binding site of hSNAP-23; wherein said second BoNT/A L-chain protease binding pocket is defined by amino acid residue Q29 of wild-type BoNT/A L-chain (SEQ ID NO: 1); and
- c) an amino acid residue change located within a fifth BoNT/A L-chain protease binding pocket for binding to the R186 binding site of hSNAP-23; wherein said fifth BoNT/A L-chain protease binding pocket is defined by amino acid residue S143 of wild-type BoNT/A L-chain (SEQ ID NO: 1);
- d) and wherein said amino acid residue change comprises:
  - i. an amino acid residue selected from the group consisting of tyrosine at the position on the modified L-chain protease amino acid sequence that corresponds to amino acid residue E148 of wild-type BoNT/A L-chain (SEQ ID NO: 1); and
  - ii. an amino acid residue selected from the group consisting of alanine at the position on the modified L-chain protease amino acid sequence that corresponds to amino acid residue Q29 of wild-type BoNT/A L-chain (SEQ ID NO: 1); and
  - iii. an amino acid residue selected from the group consisting of aspartate at the position on the modified L-chain protease amino acid sequence that corresponds to amino acid residue S143 of wild-type BoNT/A L-chain (SEQ ID NO: 1).

In another embodiment, a modified BoNT L-chain of the present invention having a binding pocket mutation for the D189/D192 binding site on hSNAP-23 can further comprise one or more mutations within at least two different BoNT/A L-chain binding pockets (e.g. within the binding pocket for the P182/D178 binding site on hSNAP-23, and within the binding pocket for the K185 binding site on hSNAP-23, as defined above). Such mutants typically demonstrate at least a 3.0-fold, preferably at least a 3.4-foldincreased hSNAP-23 cleavage (versus E148Y modified BoNT/A L-chain)—see the 1$^{st}$ data column presented for multi-pocket mutants in FIG. 1B. Examples of such modified BoNT/A L-chains (referred to by the amino acid substitution(s) relative to a corresponding wild-type BoNT/A L-chain SEQ ID NO:1) include:

a modified BoNT/A L-chain comprising the substitutions E148Y, Q29A, and G305D.

Thus, in another embodiment there is provided a modified BoNT/A L-chain protease that cleaves human SNAP-23 (hSNAP-23), and having a modified amino acid sequence relative to the wild-type BoNT/A L-chain (SEQ ID NO: 1) that comprises:
- a) an amino acid residue change located within a first BoNT/A L-chain protease binding pocket for binding to the P182/D178 binding site of hSNAP-23; wherein said first BoNT/A L-chain protease binding pocket is defined by amino acid residue E148 of wild-type BoNT/A L-chain (SEQ ID NO: 1); and
- b) an amino acid residue change located within a second BoNT/A L-chain protease binding pocket for binding to the D189/D192 binding site of hSNAP-23; wherein said second BoNT/A L-chain protease binding pocket is defined by amino acid residue Q29 of wild-type BoNT/A L-chain (SEQ ID NO: 1); and
c) an amino acid residue change located within a fourth BoNT/A L-chain protease binding pocket for binding to the K185 binding site of hSNAP-23; wherein said fourth BoNT/A L-chain protease binding pocket is defined by amino acid residue G305 of wild-type BoNT/A L-chain (SEQ ID NO: 1);
d) and wherein said amino acid residue change comprises:
  i. an amino acid residue selected from the group consisting of tyrosine at the position on the modified L-chain protease amino acid sequence that corresponds to amino acid residue E148 of wild-type BoNT/A L-chain (SEQ ID NO: 1); and
  ii. an amino acid residue selected from the group consisting of alanine at the position on the modified L-chain protease amino acid sequence that corresponds to amino acid residue Q29 of wild-type BoNT/A L-chain (SEQ ID NO: 1); and
  iii. an amino acid residue selected from the group consisting of aspartate at the position on the modified L-chain protease amino acid sequence that corresponds to amino acid residue G305 of wild-type BoNT/A L-chain (SEQ ID NO: 1).

As an additional technical feature, or as an alternative technical feature, the present invention includes BoNT/A L-chain mutants comprising one or more mutations within a herein defined pocket of the BoNT/A L-chain. By way of example, a modified BoNT/A L-chain of the present invention that cleaves human SNAP-23 (hSNAP-23) has a modified amino acid sequence relative to the wild-type BoNT/A L-chain (SEQ ID NO: 1) that comprises:
a) at least one amino acid residue change located within a sixth BoNT/A L-chain protease binding pocket for binding to the K206 binding site of hSNAP-23;
b) wherein said sixth BoNT/A L-chain protease binding pocket is defined by amino acid residues Y251, L256, V258, L367 and F369 of wild-type BoNT/A L-chain (SEQ ID NO: 1);
c) and wherein said at least one amino acid residue change comprises:
  i. an amino acid residue selected from the group consisting of glutamate and aspartate at the position on the modified L-chain protease amino acid sequence that corresponds to amino acid residue Y251 of wild-type BoNT/A L-chain (SEQ ID NO: 1); and/ or
  ii. an amino acid residue selected from the group consisting of glutamate, aspartate, glutamine, glycine, alanine and arginine at the position on the modified L-chain protease amino acid sequence that corresponds to amino acid residue L256 of wild-type BoNT/A L-chain (SEQ ID NO: 1); and/ or
  iii. an amino acid residue selected from the group consisting of serine, alanine, proline, leucine and glutamate at the position on the modified L-chain protease amino acid sequence that corresponds to amino acid residue V258 of wild-type BoNT/A L-chain (SEQ ID NO: 1); and/ or
  iv. an amino acid residue selected from the group consisting of alanine and glycine at the position on the modified L-chain protease amino acid sequence that corresponds to amino acid residue L367 of wild-type BoNT/A L-chain (SEQ ID NO: 1); and/ or
  v. an amino acid residue selected from the group consisting of glycine, serine and leucine at the position on the modified L-chain protease amino acid sequence that corresponds to amino acid residue F369 of wild-type BoNT/A L-chain (SEQ ID NO: 1).

As an additional technical feature, or as an alternative technical feature, the present invention includes BoNT/A L-chain mutants comprising one or more mutations within a herein defined pocket of the BoNT/A L-chain. By way of example, a modified BoNT/A L-chain of the present invention that cleaves human SNAP-23 (hSNAP-23) has a modified amino acid sequence relative to the wild-type BoNT/A L-chain (SEQ ID NO: 1) that comprises:
a) at least one amino acid residue change located within a sixth BoNT/A L-chain protease binding pocket for binding to the K206 binding site of hSNAP-23;
b) wherein said sixth BoNT/A L-chain protease binding pocket is defined by amino acid residues Y251, L256, V258, L367 and F369 of wild-type BoNT/A L-chain (SEQ ID NO: 1);
c) and wherein said at least one amino acid residue change comprises:
  i. an amino acid residue selected from the group consisting of glutamate and aspartate at the position on the modified L-chain protease amino acid sequence that corresponds to amino acid residue Y251 of wild-type BoNT/A L-chain (SEQ ID NO: 1); and/ or
  ii. an amino acid residue selected from the group consisting of glutamine, and arginine at the position on the modified L-chain protease amino acid sequence that corresponds to amino acid residue L256 of wild-type BoNT/A L-chain (SEQ ID NO: 1); and/ or
  iii. an amino acid residue selected from the group consisting of serine, leucine and glutamate at the position on the modified L-chain protease amino acid sequence that corresponds to amino acid residue V258 of wild-type BoNT/A L-chain (SEQ ID NO: 1); and/ or
  iv. an amino acid residue selected from the group consisting of alanine and glycine at the position on the modified L-chain protease amino acid sequence that corresponds to amino acid residue L367 of wild-type BoNT/A L-chain (SEQ ID NO: 1); and/ or
  v. an amino acid residue selected from the group consisting of glycine, serine and leucine at the position on the modified L-chain protease amino acid sequence that corresponds to amino acid residue F369 of wild-type BoNT/A L-chain (SEQ ID NO: 1).

Without wishing to be bound by any theory, Applicant believes that the above-defined BoNT/A L-chain binding pocket effects an important enzyme-substrate association with the (S3') position of the recognition sequence for hSNAP-23.

As an additional technical feature, or as an alternative technical feature, the present invention includes BoNT/A L-chain mutants comprising one or more mutations within a herein defined pocket of the BoNT/A L-chain. By way of example, a modified BoNT/A L-chain of the present invention that cleaves human SNAP-23 (hSNAP-23) has a modified amino acid sequence relative to the wild-type BoNT/A L-chain (SEQ ID NO: 1) that comprises:
a) at least one amino acid residue change located within a sixth BoNT/A L-chain protease binding pocket for binding to the K206 binding site of hSNAP-23;
b) wherein said sixth BoNT/A L-chain protease binding pocket is defined by amino acid residues Y251, L256, V258, L367 and F369 of wild-type BoNT/A L-chain (SEQ ID NO: 1);

c) and wherein said at least one amino acid residue change comprises:
  i. an amino acid residue selected from the group consisting of glutamate and aspartate at the position on the modified L-chain protease amino acid sequence that corresponds to amino acid residue Y251 of wild-type BoNT/A L-chain (SEQ ID NO: 1); and/ or
  ii. an amino acid residue selected from the group consisting of glutamine, and arginine at the position on the modified L-chain protease amino acid sequence that corresponds to amino acid residue L256 of wild-type BoNT/A L-chain (SEQ ID NO: 1); and/ or
  iii. an amino acid residue selected from the group consisting of serine, leucine and glutamate at the position on the modified L-chain protease amino acid sequence that corresponds to amino acid residue V258 of wild-type BoNT/A L-chain (SEQ ID NO: 1); and/ or
  iv. an amino acid residue selected from the group consisting of alanine and glycine at the position on the modified L-chain protease amino acid sequence that corresponds to amino acid residue L367 of wild-type BoNT/A L-chain (SEQ ID NO: 1); and/ or
  v. an amino acid residue selected from the group consisting of glycine, serine and leucine at the position on the modified L-chain protease amino acid sequence that corresponds to amino acid residue F369 of wild-type BoNT/A L-chain (SEQ ID NO: 1).

A modified BoNT/A L-chain of the present invention having a binding pocket mutation for the K206 binding site on hSNAP-23 can comprise one or more amino acid residue changes relative to the wild-type BoNT/A L-chainas herein before defined. By way of illustration, a modified BoNT/A L-chain of the present invention may have a single amino acid residue mutation (within the binding pocket for the K206 binding site on hSNAP-23), for example a mutant corresponding to amino acid residue Y251 of wild-type BoNT/A L-chain (SEQ ID NO: 1). Similarly, a modified BoNT/A L-chain of the present invention may comprise more than one mutation (within the binding pocket for the K206 binding site on hSNAP-23), for example mutants corresponding to amino acid residues Y251 & L256 of wild-type BoNT/A L-chain (SEQ ID NO: 1).

A modified BoNT/A L-chain of the present invention comprising a binding pocket mutation for the K206 binding site on hSNAP-23 typically demonstrate greater than 1.5% hSNAP-23 cleavage (% at 1 micromolar modified BoNT/A L-chain; 20 micromolar hSNAP-23; preferably incubated at about 37° C. for about 1 hour)—see the $2^{nd}$ data column in FIG. 1A. For reference, wild-type BoNT/A L-chain (e.g. SEQ ID NO: 1) demonstrates less than 0.5% hSNAP-23 cleavage (% at 1 micromolar modified BoNT/A L-chain; 20 micromolar hSNAP-23; preferably incubated at about 37° C. for about 1 hour)—see the $2^{nd}$ data column presented in FIG. 1A. Examples of such modified BoNT/A L-chains (referred to by the amino acid substitution(s) relative to a corresponding wild-type BoNT/A L-chain SEQ ID NO:1) include:

a modified BoNT/A L-chain comprising the substitution Y251D;

a modified BoNT/A L-chain comprising the substitution Y251E;

a modified BoNT/A L-chain comprising the substitution L256D.

In one embodiment, modified BoNT/A L-chains of the present invention demonstrate at least 3% hSNAP-23 cleavage (% at 1 micromolar modified BoNT/A L-chain; 20 micromolar hSNAP-23; preferably incubated at about 37° C. for about 1 hour)—see the $2^{nd}$ data column presented in FIG. 1A. Examples of such modified BoNT/A L-chains (referred to by the amino acid substitution(s) relative to a corresponding wild-type BoNT/A L-chain SEQ ID NO:1) include:

a modified BoNT/A L-chain comprising the substitution Y251E.

Additional examples of modified BoNT/A L-chain mutants having a binding pocket mutation for K206 on hSNAP-23 (referred to by the amino acid substitution(s) relative to a corresponding wild-type BoNT/A L-chain SEQ ID NO:1) include:

a modified BoNT/A L-chain comprising the substitution V245D;

a modified BoNT/A L-chain comprising the substitution L256E;

a modified BoNT/A L-chain comprising the substitution L256G;

a modified BoNT/A L-chain comprising the substitution L256Q;

a modified BoNT/A L-chain comprising the substitution L256A;

a modified BoNT/A L-chain comprising the substitution V258A;

a modified BoNT/A L-chain comprising the substitution V258P;

a modified BoNT/A L-chain comprising the substitution V258L;

a modified BoNT/A L-chain comprising the substitution L256E, and V258P;

a modified BoNT/A L-chain comprising the substitution L256Q, and V258P;

a modified BoNT/A L-chain comprising the substitution L256A, and V258L;

a modified BoNT/A L-chain comprising the substitution L256G, and V258L.

In a preferred embodiment, a modified BoNT L-chain of the present invention having a binding pocket mutation for the K206 binding site on hSNAP-23 can further comprise one or more mutations within one or more different BoNT/A L-chain binding pockets as herein described (e.g. within the binding pocket for the P182/D178 binding site on hSNAP-23, as defined above). Such mutants typically demonstrate at least a 0.5-fold decreased hSNAP-23 cleavage (versus E148Y modified BoNT/A L-chain), or, in other words at least a 4.0-fold increased hSNAP23 cleavage (versus wild-type BoNT/A L-chain)—see the $1^{st}$ data column presented for multi-pocket mutants in FIG. 1B, or at least 5 hSNAP-23 cleavage (% at 1 micromolar modified BoNT/A L-chain; 20 micromolar hSNAP-23; preferably incubated at about 37° C. for about 1 hour)—see the $2^{nd}$ data column in FIG. 1B. Preferable examples of such modified BoNT/A L-chains (referred to by the amino acid substitution(s) relative to a corresponding wild-type BoNT/A L-chain SEQ ID NO:1) include:

a modified BoNT/A L-chain comprising the substitutions E148Y, and Y251D;

a modified BoNT/A L-chain comprising the substitutions E148Y, and L256D;

a modified BoNT/A L-chain comprising the substitutions E148Y, and Y251E.

Thus, in another embodiment there is provided a modified BoNT/A L-chain protease that cleaves human SNAP-23 (hSNAP-23), and having a modified amino acid sequence relative to the wild-type BoNT/A L-chain (SEQ ID NO: 1) that comprises:

a) an amino acid residue change located within a first BoNT/A L-chain protease binding pocket for binding to the P182/D178 binding site of hSNAP-23; wherein said first BoNT/A L-chain protease binding pocket is defined by amino acid residue E148 of wild-type BoNT/A L-chain (SEQ ID NO: 1); and
b) an amino acid residue change located within a fifth BoNT/A L-chain protease binding pocket for binding to the K206 binding site of hSNAP-23; wherein said fifth BoNT/A L-chain protease binding pocket is defined by amino acid residue Y251 of wild-type BoNT/A L-chain (SEQ ID NO: 1);
c) and wherein said amino acid residue change comprises:
  i. an amino acid residue selected from the group consisting of tyrosine at the position on the modified L-chain protease amino acid sequence that corresponds to amino acid residue E148 of wild-type BoNT/A L-chain (SEQ ID NO: 1); and
  ii. an amino acid residue selected from the group consisting of aspartate at the position on the modified L-chain protease amino acid sequence that corresponds to amino acid residue Y251 of wild-type BoNT/A L-chain (SEQ ID NO: 1).

In another embodiment, a modified BoNT L-chain of the present invention having a binding pocket mutation for the K206 binding site on hSNAP-23 can further comprise one or more mutations within at least three different BoNT/A L-chain binding pockets as herein described (e.g. within the binding pocket for the P182/D178 binding site on hSNAP-23, within the binding pocket for the R186 binding site on hSNAP-23, and within the binding pocket for the D189/D192 binding site, as defined above). Such mutants typically demonstrate at least a 1.3-fold increased hSNAP-23 cleavage (versus E148Y modified BoNT/A L-chain)—see the $1^{st}$ data column presented for multi-pocket mutants in FIG. 1B. Examples of such modified BoNT/A L-chains (referred to by the amino acid substitution(s) relative to a corresponding wild-type BoNT/A L-chain SEQ ID NO:1) include:

a modified BoNT/A L-chain comprising the substitutions E148Y, S143D, Q29A, and Y251E.

Thus, in another embodiment there is provided a modified BoNT/A L-chain protease that cleaves human SNAP-23 (hSNAP-23), and having a modified amino acid sequence relative to the wild-type BoNT/A L-chain (SEQ ID NO: 1) that comprises:
a) an amino acid residue change located within a first BoNT/A L-chain protease binding pocket for binding to the P182/D178 binding site of hSNAP-23; wherein said first BoNT/A L-chain protease binding pocket is defined by amino acid residue E148 of wild-type BoNT/A L-chain (SEQ ID NO: 1); and
b) an amino acid residue change located within a fifth BoNT/A L-chain protease binding pocket for binding to the R186 binding site of hSNAP-23; wherein said fifth BoNT/A L-chain protease binding pocket is defined by amino acid residue S143 of wild-type BoNT/A L-chain (SEQ ID NO: 1); and
c) an amino acid residue change located within a second BoNT/A L-chain protease binding pocket for binding to the D189/D192 binding site of hSNAP-23; wherein said second BoNT/A L-chain protease binding pocket is defined by amino acid residue Q29A of wild-type BoNT/A L-chain (SEQ ID NO: 1); and
d) an amino acid residue change located within a sixth BoNT/A L-chain protease binding pocket for binding to the K206 binding site of hSNAP-23; wherein said sixth BoNT/A L-chain protease binding pocket is defined by amino acid residue Y251 of wild-type BoNT/A L-chain (SEQ ID NO: 1);
e) and wherein said amino acid residue change comprises:
  i. an amino acid residue selected from the group consisting of tyrosine at the position on the modified L-chain protease amino acid sequence that corresponds to amino acid residue E148 of wild-type BoNT/A L-chain (SEQ ID NO: 1); and
  ii. an amino acid residue selected from the group consisting of aspartate at the position on the modified L-chain protease amino acid sequence that corresponds to amino acid residue S143 of wild-type BoNT/A L-chain (SEQ ID NO: 1); and
  iii. an amino acid residue selected from the group consisting of alanine at the position on the modified L-chain protease amino acid sequence that corresponds to amino acid residue Q29 of wild-type BoNT/A L-chain (SEQ ID NO: 1); and
  iv. an amino acid residue selected from the group consisting of glutamate at the position on the modified L-chain protease amino acid sequence that corresponds to amino acid residue Y251 of wild-type BoNT/A L-chain (SEQ ID NO: 1).

As an additional technical feature, or as an alternative technical feature, the present invention includes BoNT/A L-chain mutants comprising one or more mutations within a herein defined pocket of the BoNT/A L-chain. By way of example, a modified BoNT/A L-chain of the present invention that cleaves human SNAP-23 (hSNAP-23) has a modified amino acid sequence relative to the wild-type BoNT/A L-chain (SEQ ID NO: 1), that comprises:
a) an amino acid residue change located within a third BoNT/A L-chain protease binding pocket for binding to the I198 binding site of hSNAP-23;
b) wherein said third BoNT/A L-chain protease binding pocket is defined by amino acid residue K166 of wild-type BoNT/A L-chain (SEQ ID NO: 1);
c) and wherein said amino acid residue change comprises:
  i. an amino acid residue selected from the group consisting of valine, phenylalanine, leucine and isoleucine at the position on the modified L-chain protease amino acid sequence that corresponds to amino acid residue K166 of wild-type BoNT/A L-chain (SEQ ID NO: 1).

Without wishing to be bound by any theory, Applicant believes that the above-defined BoNT/A L-chain binding pocket can provide a stabilising hydrophobic interaction between I198 on hSNAP-23 and amino acid 166 of BoNT/A.

Modified BoNT/A L-chains of the present invention comprising a binding pocket mutation for the I198 binding site on hSNAP-23 typically demonstrate greater than 9% hSNAP-23 cleavage (% at 1 micromolar modified BoNT/A L-chain; 20 micromolar hSNAP-23; preferably incubated at about 37° C. for about 1 hour)—see the $2^{nd}$ data column presented in FIG. 1A. For reference, wild-type BoNT/A L-chain (e.g. SEQ ID NO: 1) demonstrates less than 0.5% hSNAP-23 cleavage (% at 1 micromolar modified BoNT/A L-chain; 20 micromolar hSNAP-23; preferably incubated at about 37° C. for about 1 hour)—see the $2^{nd}$ data column presented in FIG. 1A. Examples of such modified BoNT/A L-chains (referred to by the amino acid substitution(s) relative to a corresponding wild-type BoNT/A L-chain SEQ ID NO:1) include:

a modified BoNT/A L-chain comprising the substitution K166V;

a modified BoNT/A L-chain comprising the substitution K166F;

a modified BoNT/A L-chain comprising the substitution K166L;

a modified BoNT/A L-chain comprising the substitution K166I.

In one embodiment, modified BoNT/A L-chains of the present invention comprising a binding pocket mutation for the I198 binding site on hSNAP-23 typically demonstrate greater than 40% hSNAP-23 cleavage (% at 1 micromolar modified BoNT/A L-chain; 20 micromolar hSNAP-23; preferably incubated at about 37° C. for about 1 hour)—see the $2^{nd}$ data column presented in FIG. 1A. Examples of such modified BoNT/A L-chains (referred to by the amino acid substitution(s) relative to a corresponding wild-type BoNT/A L-chain SEQ ID NO:1) include:

a modified BoNT/A L-chain comprising the substitution K166F;

a modified BoNT/A L-chain comprising the substitution K166L.

In a further embodiment, modified BoNT/A L-chains of the present invention comprising a binding pocket mutation for the I198 binding site on hSNAP-23 typically demonstrate greater than 60% hSNAP-23 cleavage (% at 1 micromolar modified BoNT/A L-chain; 20 micromolar hSNAP-23; preferably incubated at about 37° C. for about 1 hour)—see the $2^{nd}$ data column presented in FIG. 1A. Examples of such modified BoNT/A L-chains (referred to by the amino acid substitution(s) relative to a corresponding wild-type BoNT/A L-chain SEQ ID NO:1) include:

a modified BoNT/A L-chain comprising the substitution K166F.

In a preferred embodiment, a modified BoNT L-chain of the present invention having a binding pocket mutation for the I198 binding site on hSNAP-23 can further comprise one or more mutations within one or more different BoNT/A L-chain binding pockets as herein described (for example, within at least two different BoNT/A L-chain binding pockets such as the binding pocket for the P182/D178 binding site on hSNAP-23, and the binding pocket for the K185 or R186 binding site on hSNAP-23). Such mutants typically demonstrate at least 40% hSNAP-23 cleavage (% at 1 micromolar modified BoNT/A L-chain; 20 micromolar hSNAP-23; preferably incubated at about 37° C. for about 1 hour)—see the $2^{nd}$ data column presented in FIG. 1B. Examples of such modified BoNT/A L-chains (referred to by the amino acid substitution(s) relative to a corresponding wild-type BoNT/A L-chain SEQ ID NO:1) include:

a modified BoNT/A L-chain comprising the substitutions E148Y, K166F, and G305D;

a modified BoNT/A L-chain comprising the substitutions E148Y, K166V, and G305D;

a modified BoNT/A L-chain comprising the substitutions E148Y, S143D, and K166F.

Thus, in another embodiment there is provided a modified BoNT/A L-chain protease that cleaves human SNAP-23 (hSNAP-23), and having a modified amino acid sequence relative to the wild-type BoNT/A L-chain (SEQ ID NO: 1) that comprises:

a) an amino acid residue change located within a first BoNT/A L-chain protease binding pocket for binding to the P182/D178 binding site of hSNAP-23; wherein said first BoNT/A L-chain protease binding pocket is defined by amino acid residue E148 of wild-type BoNT/A L-chain (SEQ ID NO: 1); and b) an amino acid residue change located within a third BoNT/A L-chain protease binding pocket for binding to the I198 binding site of hSNAP-23; wherein said third BoNT/A L-chain protease binding pocket is defined by amino acid residue K166 of wild-type BoNT/A L-chain (SEQ ID NO: 1); and c) an amino acid residue change located within a fourth BoNT/A L-chain protease binding pocket for binding to the K185 binding site of hSNAP-23; wherein said fourth BoNT/A L-chain protease binding pocket is defined by amino acid residue G305 of wild-type BoNT/A L-chain (SEQ ID NO: 1);

d) and wherein said amino acid residue change comprises:
  i. an amino acid residue selected from the group consisting of tyrosine at the position on the modified L-chain protease amino acid sequence that corresponds to amino acid residue E148 of wild-type BoNT/A L-chain (SEQ ID NO: 1); and
  ii. an amino acid residue selected from the group consisting of valine at the position on the modified L-chain protease amino acid sequence that corresponds to amino acid residue K166 of wild-type BoNT/A L-chain (SEQ ID NO: 1); and
  iii. an amino acid residue selected from the group consisting of aspartate at the position on the modified L-chain protease amino acid sequence that corresponds to amino acid residue G305 of wild-type BoNT/A L-chain (SEQ ID NO: 1).

In another embodiment, a modified BoNT L-chain of the present invention having a binding pocket mutation for the I198 binding site on hSNAP-23 can further comprise one or more mutation(s) within at least two different BoNT/A L-chain binding pockets (e.g. within the binding pocket for the P182/D178 binding site on hSNAP-23, and within the binding pocket for the K185 or R186 binding site on hSNAP-23). Such mutants typically demonstrate at least 15% hSNAP-23 cleavage (% at 10 nanomolar modified BoNT/A L-chain; 20 micromolar hSNAP-23; preferably incubated at about 37° C. for about 1 hour)—see the $2^{nd}$ data column ** presented in FIG. 1B. Examples of such modified BoNT/A L-chains (referred to by the amino acid substitution(s) relative to a corresponding wild-type BoNT/A L-chain SEQ ID NO:1) include:

a modified BoNT/A L-chain comprising the substitution E148Y, K166F, and G305D;

a modified BoNT/A L-chain comprising the substitution E148Y, S143D, and K166F.

In one embodiment, a modified BoNT L-chain of the present invention having a binding pocket mutation for the I198 binding site on hSNAP-23 can further comprise one or more mutations within at least three different BoNT/A L-chain binding pockets (e.g. within the binding pocket for the P182/D178 binding site on hSNAP-23, within the binding pocket for the D189/D192 binding site on hSNAP23, and within the binding pocket for the K185 binding site on hSNAP-23, as defined above). Such mutants typically demonstrate at least 60% hSNAP-23 cleavage (% at 1 micromolar modified BoNT/A L-chain; 20 micromolar hSNAP-23; preferably incubated at about 37° C. for about 1 hour)—see the $2^{nd}$ data column presented in FIG. 1B. Examples of such modified BoNT/A L-chains (referred to by the amino acid substitution(s) relative to a corresponding wild-type BoNT/A L-chain SEQ ID NO:1) include:

a modified BoNT/A L-chain comprising the substitutions E148Y, Q29A, K166V, and G305D;

a modified BoNT/A L-chain comprising the substitutions E148Y, Q29A, K166F, and G305D.

Thus, in another embodiment there is provided a modified BoNT/A L-chain protease that cleaves human SNAP-23

(hSNAP-23), and having a modified amino acid sequence relative to the wild-type BoNT/A L-chain (SEQ ID NO: 1) that comprises:
  a) an amino acid residue change located within a first BoNT/A L-chain protease binding pocket for binding to the P182/D178 binding site of hSNAP-23; wherein said first BoNT/A L-chain protease binding pocket is defined by amino acid residue E148 of wild-type BoNT/A L-chain (SEQ ID NO: 1); and
  b) an amino acid residue change located within a third BoNT/A L-chain protease binding pocket for binding to the 1198 binding site of hSNAP-23; wherein said third BoNT/A L-chain protease binding pocket is defined by amino acid residue K166 of wild-type BoNT/A L-chain (SEQ ID NO: 1); and
  c) an amino acid residue change located within a second BoNT/A L-chain protease binding pocket for binding to the D189/D192 binding site of hSNAP-23; wherein said second BoNT/A L-chain protease binding pocket is defined by amino acid residue Q29A of wild-type BoNT/A L-chain (SEQ ID NO: 1); and
  d) an amino acid residue change located within a fourth BoNT/A L-chain protease binding pocket for binding to the K185 binding site of hSNAP-23; wherein said fourth BoNT/A L-chain protease binding pocket is defined by amino acid residue G305 of wild-type BoNT/A L-chain (SEQ ID NO: 1);
  e) and wherein said amino acid residue change comprises:
    i. an amino acid residue selected from the group consisting of tyrosine at the position on the modified L-chain protease amino acid sequence that corresponds to amino acid residue E148 of wild-type BoNT/A L-chain (SEQ ID NO: 1); and
    ii. an amino acid residue selected from the group consisting of valine at the position on the modified L-chain protease amino acid sequence that corresponds to amino acid residue K166 of wild-type BoNT/A L-chain (SEQ ID NO: 1); and
    iii. an amino acid residue selected from the group consisting of alanine at the position on the modified L-chain protease amino acid sequence that corresponds to amino acid residue Q29 of wild-type BoNT/A L-chain (SEQ ID NO: 1); and
    iv. an amino acid residue selected from the group consisting of aspartate at the position on the modified L-chain protease amino acid sequence that corresponds to amino acid residue G305 of wild-type BoNT/A L-chain (SEQ ID NO: 1).

In another embodiment, a modified BoNT L-chain of the present invention having a binding pocket mutation for the 1198 binding site on hSNAP-23 can further comprise one or more mutations within at least three different BoNT/A L-chain binding pockets (e.g. within the binding pocket for the P182 /D178 binding site on hSNAP-23, within the binding pocket for the D189/D192 binding site on hSNAP23, and within the binding pocket for the K185 binding site on hSNAP-23). Such mutants typically demonstrate at least 10% hSNAP-23 cleavage (% at 10 nanomolar modified BoNT/A L-chain; 20 micromolar hSNAP-23; preferably incubated at about 37° C. for about 1 hour)—see the $2^{nd}$ data column ** presented in FIG. 1B. Examples of such modified BoNT/A L-chains (referred to by the amino acid substitution(s) relative to a corresponding wild-type BoNT/A L-chain SEQ ID NO:1) include:
  a modified BoNT/A L-chain comprising the substitution E148Y, Q29A, K166F, and G305D.

Additional examples of modified BoNT/A L-chain mutants having a binding pocket mutation for 1198 on hSNAP-23 (referred to by the amino acid substitution(s) relative to a corresponding wild-type BoNT/A L-chain SEQ ID NO:1) include:
  a modified BoNT/A L-chain comprising the substitution E148Y, Q29A, K166F, Y251 E, and G305D.

In one embodiment, a modified BoNT L-chain of the present invention having a binding pocket mutation for the 1198 binding site on hSNAP-23 can further comprise one or more mutations within one or more different BoNT/A L-chain binding pockets (e.g. within the binding pocket for the P182/D178 binding site on hSNAP-23, or within the binding pocket for the K185 binding site on hSNAP-23, as defined above). Such mutants typically demonstrate at least 3% hSNAP-23 cleavage (% at 10 nanomolar modified BoNT/A L-chain; 20 micromolar hSNAP-23; preferably incubated at about 37° C. for about 1 hour)—see the $2^{nd}$ data column ** presented in FIG. 1B. Examples of such modified BoNT/A L-chains (referred to by the amino acid substitution(s) relative to a corresponding wild-type BoNT/A L-chain SEQ ID NO:1) include:
  a modified BoNT/A L-chain comprising the substitution E148Y, and K166F;
  a modified BoNT/A L-chain comprising the substitution G305D, and K166F.

In another embodiment, a modified BoNT L-chain of the present invention having a binding pocket mutation for the 1198 binding site on hSNAP-23 can further comprise one or more mutation(s) within one or more different BoNT/A L-chain binding pockets (e.g. within the binding pocket for the P182 /D178 binding site on hSNAP-23, or within the binding pocket for the K185 binding site on hSNAP-23). Such mutants typically demonstrate at least 5% hSNAP-23 cleavage (% at 10 nanomolar modified BoNT/A L-chain; 20 micromolar hSNAP-23; preferably incubated at about 37° C. for about 1 hour)—see the $2^{nd}$ data column ** presented in FIG. 1B. Examples of such modified BoNT/A L-chains (referred to by the amino acid substitution(s) relative to a corresponding wild-type BoNT/A L-chain SEQ ID NO:1) include:
  a modified BoNT/A L-chain comprising the substitution E148Y, and K166F.

As an additional technical feature, or as an alternative technical feature, the present invention includes BoNT/A L-chain mutants comprising one or more mutations within a herein defined pocket of the BoNT/A L-chain. By way of example, a modified BoNT/A L-chain of the present invention that cleaves human SNAP-23 (hSNAP-23) has a modified amino acid sequence relative to the wild-type BoNT/A L-chain (SEQ ID NO: 1), that comprises:
  a) an amino acid residue change located within a seventh BoNT/A L-chain protease binding pocket for binding to the D210 binding site of hSNAP-23;
  b) wherein said seventh BoNT/A L-chain protease binding pocket is defined by amino acid residue S254 of wild-type BoNT/A L-chain (SEQ ID NO: 1);
  c) and wherein said amino acid residue change comprises:
    i. an (e.g. the) amino acid residue alanine at the position on the modified L-chain protease amino acid sequence that corresponds to amino acid residue S254 of wild-type BoNT/A L-chain (SEQ ID NO: 1).

Without wishing to be bound by any theory, Applicant believes that the above-defined BoNT/A L-chain binding pocket can exhibit hydrogen bonding with the D210 binding site of hSNAP-23. Moreover, Applicant believes modification of said binding pocket (as herein defined) precludes a hydrogen bond proposed to be formed between D210 on hSNAP-23 and amino acid 254 of BoNT/A. This is, in turn, believed to generate a C-terminal hSNAP-23 cleavage product in the form of a better "leaving group", and thereby enhance the hSNAP-23 cleavage rate.

Examples of such modified BoNT/A L-chains (referred to by the amino acid substitution(s) relative to a corresponding wild-type BoNT/A L-chain SEQ ID NO:1) include:

a modified BoNT/A L-chain comprising the substitution S254A.

In one embodiment, a modified BoNT L-chain of the present invention having a binding pocket mutation for the D210 binding site on hSNAP-23 can further comprise one or more mutations within one or more different BoNT/A L-chain binding pockets as herein described (for example, within at least two or three different BoNT/A L-chain binding pockets such as the binding pocket for the P182/D178 binding site on hSNAP-23, and the binding pocket for the 1198 binding site on hSNAP-23, and optionally the binding pocket for the K185 binding site on hSNAP23). Such mutants typically demonstrate at least 10% hSNAP-23 cleavage (% at 10 nanomolar modified BoNT/A L-chain; 20 micromolar hSNAP-23; preferably incubated at about 37° C. for about 1 hour)—see the $2^{nd}$ data column ** presented in FIG. 1B. Examples of such modified BoNT/A L-chains include:

a modified BoNT/A L-chain comprising the substitution E148Y, K166F, and 5254A;

a modified BoNT/A L-chain comprising the substitution E148Y, K166F, S254A, and G305D.

In a preferred embodiment, a modified BoNT L-chain of the present invention having a binding pocket mutation for the D210 binding site on hSNAP-23 can further comprise one or more mutations within one or more different BoNT/A L-chain binding pockets as herein described (for example, within at least three different BoNT/A L-chain binding pockets such as the binding pocket for the P182/D178 binding site on hSNAP-23, the binding pocket for the 1198 binding site on hSNAP-23, and the binding pocket for the K185 binding site on hSNAP23). Such mutants typically demonstrate at least 25% hSNAP-23 cleavage (% at 10 nanomolar modified BoNT/A L-chain; 20 micromolar hSNAP-23; preferably incubated at about 37° C. for about 1 hour)—see the $2^{nd}$ data column ** presented in FIG. 1B. Examples of such modified BoNT/A L-chains (referred to by the amino acid substitution(s) relative to a corresponding wild-type BoNT/A L-chain SEQ ID NO:1) include:

a modified BoNT/A L-chain comprising the substitution E148Y, K166F, S254A, and G305D.

As an additional technical feature, or as an alternative technical feature, the present invention includes BoNT/A L-chain mutants comprising one or more mutations within a herein defined pocket of the BoNT/A L-chain. By way of example, a modified BoNT/A L-chain of the present invention that cleaves human SNAP-23 (hSNAP-23) has a modified amino acid sequence relative to the wild-type BoNT/A L-chain (SEQ ID NO: 1), that comprises:
  a) an amino acid residue change located within an eighth BoNT/A L-chain protease binding pocket for binding to the D168 binding site of hSNAP-23;
  b) wherein said eighth BoNT/A L-chain protease binding pocket is defined by amino acid residue K340 of wild-type BoNT/A L-chain (SEQ ID NO: 1);
  c) and wherein said amino acid residue change comprises:
    i. an (e.g. the) amino acid residue histidine at the position on the modified L-chain protease amino acid sequence that corresponds to amino acid residue K340 of wild-type BoNT/A L-chain (SEQ ID NO: 1).

Without wishing to be bound by any theory, Applicant believes that the above-defined BoNT/A L-chain binding pocket can provide a salt bridge between D168 on hSNAP-23 and amino acid 340 of BoNT/A.

Examples of such modified BoNT/A L-chains (referred to by the amino acid substitution(s) relative to a corresponding wild-type BoNT/A L-chain SEQ ID NO:1) include:

a modified BoNT/A L-chain comprising the substitution K340H.

In one embodiment, a modified BoNT L-chain of the present invention having a binding pocket mutation for the P182/D178 binding site on hSNAP-23 can further comprise one or more mutations within the BoNT/A L-chain binding pocket for the D168 binding site on hSNAP-23. Such mutants typically demonstrate at least 3% hSNAP-23 cleavage (% at 1 micromolar modified BoNT/A L-chain; 20 micromolar hSNAP-23; preferably incubated at about 37° C. for about 1 hour)—see the $2^{nd}$ data column presented in FIG. 1B.

Examples of such modified BoNT/A L-chains (referred to by the amino acid substitution(s) relative to a corresponding wild-type BoNT/A L-chain SEQ ID NO:1) include:

a modified BoNT/A L-chain comprising the substitution E148Y, and K340H.

The modified BoNT/A L-chain protease as described above can comprise an amino acid sequence having at least 70%, for example, at least 80% or at least 85% or at least 90% or at least 95% or at least 97% or at least 98% or at least 99%, sequence identity to the wild-type BoNT/A L-chain (SEQ ID NO: 1). The modified BoNT/A L-chain amino acid sequence has less than 100% sequence identity to a wild-type BoNT/A L-chain (e.g. SEQ ID NO: 1). As previously indicated, reference through this specification to a modified BoNT/A L-chain protease embraces functional fragments thereof, that is fragments of said protease that cleave hSNAP-23. For example, a modified BoNT/A L-chain protease of the invention comprises at least 300 (for example, at least 350 or at least 400 or at least 410) amino acids. By way of example, the N-terminal eight amino acids and/ or the carboxyl-terminus (for example, the last 32 amino acids) of a botulinum neurotoxin L-chain protease are not required for proteolytic activity.

A modified BoNT/A L-chain of the present invention may be PEGylated to increase stability, for example duration of action of the protease component. PEGylation preferably includes the addition of PEG to the N-terminus of the L-chain. By way of example, the N-terminus of the L-chain may be extended with one or more amino acid (e.g. cysteine) residues. One or more of said amino acid residues may have its own PEG molecule attached (e.g. covalently attached) thereto. An example of this technology is described in WO2007/104567, which is incorporated in its entirety by reference thereto.

A modified BoNT/A L-chain of the present invention may include the addition (or removal) of "secondary modification sites"—see WO2002/040506, US7223577 and WO2005/068494, each of which is incorporated in its entirety by reference thereto. The additional presence or absence (vis-a-vis wild-type BoNT L-chain) of such sites alters the biological persistence (e.g. biological half-life) of a modified L-chain of the invention.

A second aspect of the present invention provides a nucleic acid construct, comprising or consisting of a nucleic acid sequence that encodes a modified BoNT/A L-chain as herein described. Said nucleic acid sequence may preferably encode a TSI delivery vehicle as further described below. A nucleic acid construct of the invention may include conventional regulatory elements such as a promoter and/or a terminator.

In one embodiment, the nucleic acid construct is provided in the form of a bacterial plasmid or viral vector. Said nucleic acid contruct can optionally be codon-biased for optimizing expression (e.g. recombinant expression) in a desired host cell (e.g. E. coli).

In one embodiment, a nucleic acid construct encoding a modified BoNT/A L-chain as herein described can be employed for administration to a target cell of interest, such as for therapeutic or cosmetic purpose. To this end, said nucleic acid construct can be typically optimised by way of conventional methodology for delivery into (followed by expression within) a target cell, preferably a human cell. The target cell is preferably a non-neuronal cell.

A third aspect of the present invention provides a delivery vehicle for the modified BoNT/A L-chain, thereby facilitating entry of the modified BoNT/A L-chain into a target cell of interest. According to this aspect, the invention more specifically relates to a delivery vehicle, comprising:
  a) a modified BoNT/A L chain protease according to the invention, or a nucleic acid construct comprising or consisting of a nucleic acid sequence encoding a modified BoNT/A L-chain according to the invention; and
  b) means for delivering said modified BoNT/A L chain protease, or said nucleic acid construct, to a target cell.

Preferred means for such delivery include any conventional delivery vehicle technique known in the art, such as liposomes, biolistic particles, cell-penetrating peptides, gene transfer vectors, etc.

One particularly preferred delivery technique that is highly suited for use with the present invention is Applicant's proprietory Targeted Secretion Inhibitor (TSI) technology. The basic methods employed to generate a TSI are well documented and now considered conventional (see for example, WO98/07864, WO2006/059113, WO2009/150469, WO2010/020811, WO2009/150470, WO2010/094905, WO2012/156743, each of which is incorporated by reference in its entirety). TSI technology relies on a delivery mechanism that mimics the same basic steps employed by a clostridial neurotoxin when it intoxicates a host cell (i.e. binding to a target cell, endosome formation, translocation of L-chain into the cytosol, proteolytic cleavage of SNARE protein by the L-chain). TSI delivery vehicles are based on a simple clostridial neurotoxin backbone having three principal components:
  1) a clostridial neurotoxin L-chain;
  2) a Targeting Moiety (TM) to direct the delivery vehicle to a target cell of choice. Typically, the native clostridial neurotoxin binding domain ($H_{CC}$) can be replaced by a ligand to provide selective binding of the delivery vehicle to a desired target cell other than the native target cell of said $H_{CC}$. In a preferred embodiment, more that one TM can be used (optionally including clostridial neurotoxin binding domain);
  3) a translocation peptide (e.g. a clostridial neurotoxin $H_N$ translocation domain) to ensure delivery of the clostridial neurotoxin L-chain into a target cell where it can then exert its proteolytic effect (i.e. cleavage of a SNARE protein).

Thus, in a preferred embodiment, the means b) of the delivery vehicle of the invention may comprise:
  i) a Targeting Moiety (TM) that binds the delivery vehicle to a target cell. Said Targeting Moeity can either be a native clostridial neurotoxin binding domain ($H_{CC}$) or, more preferably, a ligand providing binding to a target cell other than the native target cell of said $H_{CC}$; and
  ii) a translocation peptide that translocates the modified BoNT/A L chain protease of the invention into the target cell, preferably into the cytosol of said cell.

A delivery vehicle of the present invention typically includes one or more Targeting Moiety (TM). Reference to a TM embraces any structure (typically a peptide) that functionally interacts with a Site (e.g. a receptor or acceptor) to cause a physical association between the modified BoNT/A L-chain protease of the invention and the surface of a mammalian target cell (e.g. a human cell). The Site is preferably one that is capable of internalisation (e.g. endosome formation)—also referred to as receptor-mediated endocytosis. The TM may possess an endosomal membrane translocation function, in which case separate TM and Translocation Domain components need not be employed.

The TM of the present invention binds (e.g. specifically binds) to a target cell of choice. The term "specifically binds" preferably means that a given TM binds to the target cell with a binding affinity (Ka) of $10^6$ $M^{-1}$ or greater, for example $10^7$ $M^{-1}$ or greater, $10^8$ $M^{-1}$ or greater, or $10^9$ $M^{-1}$ or greater.

It is routine to confirm that a TM binds to the selected target cell. For example, a simple radioactive displacement experiment may be employed in which tissue or cells representative of a target cell of interest are exposed to labelled (eg. tritiated) TM in the presence of an excess of unlabelled TM. In such an experiment, the relative proportions of non-specific and specific binding may be assessed, thereby allowing confirmation that the TM binds to the target cell. Optionally, the assay may include one or more binding antagonists, and the assay may further comprise observing a loss of TM binding. Examples of this type of experiment can be found in Hulme, E. C. (1990), Receptor-binding studies, a brief outline, pp. 303-311, In Receptor biochemistry, A Practical Approach, Ed. E. C. Hulme, Oxford University Press.

A TM of the present invention preferably binds to a non-neuronal target cell (e.g. a mast cell and/ or an epithelial cell—see, for example WO00/10598 and WO01/21213, each of which is incorporated in its entirety by reference thereto). In doing so, said TM is able to direct the delivery vehicle to a chosen non-neuronal target cell that is expressing an undesired hSNAP-23 phenotype (and optionally an undesired SNAP-25 phenotype). In parallel, a TM of the present invention may separately bind (e.g. via the same TM or via a second TM) to a second target cell of choice, for example to a second non-neuronal target cell or to a neuronal target cell expressing an undesired hSNAP-23 and/or SNAP-25 phenotype.

Suitable TMs include: ligands to mammalian cell Binding Sites receptors such as cytokines, growth factors, neuropeptides, lectins, and antibodies—this term includes monoclonal antibodies, single-chain antibodies, and antibody fragments such as Fab, F(ab)'$_2$, Fv, ScFv, etc.

By way of further example, TMs include a leptin peptide, a ghrelin receptor, a somatostatin peptide, an insulin growth factor peptide, an ErbB peptide (e.g. EGF), a VIP-glucagon-GRF-secretin peptide (e.g. a PACAP peptide), an interleukin peptide (e.g. Il-1, IL-2, IL-6 or IL-10 peptide), a NGF peptide, a VEGF peptide, a bombesin peptide, a urotensin peptide, a melanin-concentrating hormone peptide, a prolactin releasing hormone peptide, a KiSS-1 peptide, a CRF peptide, a GHRH peptide, a substance P peptide, a beta-2 adrenoreceptor peptide, a gastrin-releasing peptide, a calcitonin gene-related peptide, a platelet-derived growth factor peptide, a keratinocyte growth factor peptide, a hepatocyte growth factor peptide, a TGF-alpha peptide, a TGF-beta peptide, an atrial natriuretic peptide, and an integrin peptide.

A delivery vehicle of the invention typically lacks a (functional) clostridial neurotoxin binding domain (as a TM).

Alternatively, a delivery vehicle of the invention may include a (functional) clostridial neurotoxin binding domain (as a TM). Reference to a clostridial neurotoxin binding domain embraces the $H_C$ (more precisely, the $H_{CC}$) part of a clostridial neurotoxin, as well as mutants thereof that retain a binding capability of the $H_C$ domain (e.g. to bind rat synaptosomal membranes in conventional binding assays such as described in Shone et al. (1985) Eur. J. Biochem. 151, 75-82).

The $H_C$ binding domain/peptide of a native clostridial neurotoxin comprises approximately 400-440 amino acid residues, and consists of two functionally distinct domains of approximately 25 kDa each, namely the N-terminal region (commonly referred to as the $H_{CN}$ peptide or domain) and the C-terminal region (commonly referred to as the $H_{CC}$ peptide or domain). It is the C-terminal region ($H_{CC}$), which constitutes the C-terminal 160-200 amino acid residues, that is responsible for binding of a clostridial neurotoxin (to nerve terminals at the neuromuscular junction). Exemplary $H_{CC}$ peptides include:

Botulinum type A neurotoxin—amino acid residues (Y1111-L1296)
Botulinum type B neurotoxin—amino acid residues (Y1098-E1291)
Botulinum type C neurotoxin—amino acid residues (Y1112-E1291)
Botulinum type D neurotoxin—amino acid residues (Y1099-E1276)
Botulinum type E neurotoxin—amino acid residues (Y1086-K1252)
Botulinum type F neurotoxin—amino acid residues (Y1106-E1274)
Botulinum type G neurotoxin—amino acid residues (Y1106-E1297)
Tetanus neurotoxin—amino acid residues (Y1128-D1315).

The above-identified reference sequences should be considered a guide, as slight variations may occur according to sub-serotypes.

A delivery vehicle of the present invention typically includes a translocation peptide, which enables translocation of the modified L-chain into the cytosol of a target. Whether a peptide possesses the requisite translocation function of the present invention may be confirmed by any one of a number of conventional assays. For example, Shone C. (1987) describes an in vitro assay employing liposomes, which are challenged with a test molecule.

Presence of the requisite translocation function is confirmed by release from the liposomes of $K^+$ and/or labelled NAD, which may be readily monitored [see Shone C. (1987) Eur. J. Biochem; vol. 167(1): pp. 175-180]. A further example is provided by Blaustein R. (1987), which describes a simple in vitro assay employing planar phospholipid bilayer membranes. The membranes are challenged with a test molecule and the requisite translocation function is confirmed by an increase in conductance across said membranes [see Blaustein (1987) FEBS Letts; vol. 226, no. 1: pp. 115-120]. Additional methodology to enable assessment of membrane fusion and thus identification of Translocation Domains suitable for use in the present invention are provided by Methods in Enzymology Vol 220 and 221, Membrane Fusion Techniques, Parts A and B, Academic Press 1993.

The Translocation Domain may be of a clostridial origin, such as the $H_N$ domain/portion of a neurotoxin. Reference to a "$H_N$ domain" means a fragment of the H-chain of a clostridial neurotoxin approximately equivalent to the amino-terminal half of the H-chain. A $H_N$ domain of a clostridial neurotoxin lacks the natural binding function of the $H_C$ component of the H-chain. Thus, a $H_N$ domain is incapable of binding to the Binding Site on a target cell to which native clostridial neurotoxin (i.e. holotoxin) binds.

Examples of suitable (reference) Translocation Domains include:
Botulinum type A neurotoxin—amino acid residues (449-871)
Botulinum type B neurotoxin—amino acid residues (441-858)
Botulinum type C neurotoxin—amino acid residues (442-866)
Botulinum type D neurotoxin—amino acid residues (446-862)
Botulinum type E neurotoxin—amino acid residues (423-845)
Botulinum type F neurotoxin—amino acid residues (440-864)
Botulinum type G neurotoxin—amino acid residues (442-863)
Tetanus neurotoxin—amino acid residues (458-879)

Research has shown that the entire length of a $H_N$ portion from a clostridial neurotoxin heavy chain is not necessary for translocation activity. Thus, aspects of this embodiment can include clostridial toxin $H_N$ regions comprising a translocation domain having a length of, for example, at least 350 amino acids, at least 375 amino acids, at least 400 amino acids and at least 425 amino acids. For further details on the genetic basis of toxin production in *Clostridium botulinum* and *C. tetani*, we refer to Henderson et al (1997) in *The Clostridia: Molecular Biology and Pathogenesis*, Academic press.

The term $H_N$ embraces naturally-occurring neurotoxin $H_N$ portions as well as variant $H_N$ portions having amino acid sequences that do not occur in nature so long as the variant $H_N$ portions still demonstrate the above-mentioned translocation function. For example, a clostridial neurotoxin $H_N$ portion embraces variant amino acid sequences having at least 70% (for example, at least 80% or at least 85% or at least 90% or at least 95% or at least 97% or at least 98% or at least 99%) sequence identity to a wild-type clostridial neurotoxin $H_N$ portion, though with the proviso that a translocation function is retained.

Alternatively, the translocation peptide may be of a non-clostridial origin, for example, the translocation domain of diphtheria toxin [O. Keefe et al., Proc. Natl. Acad. Sci. USA (1992) 89, 6202-6206; Silverman et al., J. Biol. Chem. (1993) 269, 22524-22532; and London, E. (1992) *Biochem. Biophys. Acta.*, 1112, pp.25-51], the translocation domain of *Pseudomonas* exotoxin type A [Prior et al. Biochemistry (1992) 31, 3555-3559], the translocation domains of anthrax toxin [Blanke et al. Proc. Natl. Acad. Sci. USA (1996) 93, 8437-8442], a variety of fusogenic or hydrophobic peptides of translocating function [Plank et al. J. Biol. Chem. (1994) 269, 12918-12924; and Wagner et al (1992) *PNAS*, 89, pp.7934-7938], and amphiphilic peptides [Murata et al (1992) *Biochem.*, 31, pp.1986-1992].

Reference to non-clostridial neurotoxin translocation peptides embraces fragment and variant amino acid sequences having at least 70% (for example, at least 80% or at least 85% or at least 90% or at least 95% or at least 97% or at least 98% or at least 99%) sequence identity to the corresponding non-clostridial wild-type translocation peptide sequence, though with proviso that the variant possesses the requisite.

| Translocation Domain source | Amino acid residues | References |
|---|---|---|
| Diphtheria toxin | 194-380 | Silverman et al., 1994, J. Biol. Chem. 269, 22524-22532<br>London E., 1992, Biochem. Biophys. Acta., 1113, 25-51 |
| Domain II of pseudomonas exotoxin | 405-613 | Prior et al., 1992, Biochemistry 31, 3555-3559<br>Kihara & Pastan, 1994, Bioconj Chem. 5, 532-538 |
| Influenza virus haemagglutinin | GLFGAIAGFIENGWE GMIDGWYG (SEQ ID NO: 12), and Variants thereof | Plank et al., 1994, J. Biol. Chem. 269, 12918-12924<br>Wagner et al., 1992, PNAS, 89, 7934-7938<br>Murata et al., 1992, Biochemistry 31, 1986-1992 |
| Semliki Forest virus fusogenic protein | Translocation domain | Kielian et al., 1996, J Cell Biol. 134(4), 863-872 |
| Vesicular Stomatitis virus glycoprotein G | 118-139 | Yao et al., 2003, Virology 310(2), 319-332 |
| SER virus F protein | Translocation domain | Seth et al., 2003, J Virol 77(11) 6520-6527 |
| Foamy virus envelope glycoprotein | Translocation domain | Picard-Maureau et al., 2003, J Virol. 77(8), 4722-4730 |

The polypeptides of the present invention may further comprise a translocation facilitating domain. Said domain facilitates delivery of the non-cytotoxic protease into the cytosol of the target cell and are described, for example, in WO 08/008803 and WO 08/008805, each of which is herein incorporated by reference thereto.

By way of example, suitable translocation facilitating domains include an enveloped virus fusogenic peptide domain, for example, suitable fusogenic peptide domains include influenzavirus fusogenic peptide domain (eg. influenza A virus fusogenic peptide domain of 23 amino acids), alphavirus fusogenic peptide domain (eg. Semliki Forest virus fusogenic peptide domain of 26 amino acids), vesiculovirus fusogenic peptide domain (eg. vesicular stomatitis virus fusogenic peptide domain of 21 amino acids), respirovirus fusogenic peptide domain (eg. Sendai virus fusogenic peptide domain of 25 amino acids), morbiliivirus fusogenic peptide domain (eg. Canine distemper virus fusogenic peptide domain of 25 amino acids), avulavirus fusogenic peptide domain (eg. Newcastle disease virus fusogenic peptide domain of 25 amino acids), henipavirus fusogenic peptide domain (eg. Hendra virus fusogenic peptide domain of 25 amino acids), metapneumovirus fusogenic peptide domain (eg. Human metapneumovirus fusogenic peptide domain of 25 amino acids) or spumavirus fusogenic peptide domain such as simian foamy virus fusogenic peptide domain; or fragments or variants thereof.

By way of further example, a translocation facilitating domain may comprise a clostridial neurotoxin $H_{CN}$ domain or a fragment or variant (having at least 70% sequence identity to the corresponding wild-type sequence), though with the proviso that an enhanced translocation function is retained. In more detail, a Clostridial toxin $H_{CN}$ translocation facilitating domain may have a length of at least 200 amino acids, at least 225 amino acids, at least 250 amino acids, at least 275 amino acids. In this regard, a Clostridial toxin $H_{CN}$ translocation facilitating domain preferably has a length of at most 200 amino acids, at most 225 amino acids, at most 250 amino acids, or at most 275 amino acids. Specific (reference) examples include:

Botulinum type A neurotoxin—amino acid residues (872-1110)
Botulinum type B neurotoxin—amino acid residues (859-1097)
Botulinum type C neurotoxin—amino acid residues (867-1111)
Botulinum type D neurotoxin—amino acid residues (863-1098)
Botulinum type E neurotoxin—amino acid residues (846-1085)
Botulinum type F neurotoxin—amino acid residues (865-1105)
Botulinum type G neurotoxin—amino acid residues (864-1105)
Tetanus neurotoxin—amino acid residues (880-1127).

A fourth aspect of the present invention provides a method of cleaving hSNAP-23, said method comprising contacting hSNAP-23 with a modified BoNT/A L-chain protease, or with a nucleic acid construct, or with a delivery vehicle, as herein described, thereby allowing the modified BoNT/A L-chain to bind said hSNAP-23, followed by proteolytic cleavage of the hSNAP-23 by the modified BoNT/A L-chain protease. In one embodiment, said method is performed in vitro.

In one embodiment, said method of cleaving hSNAP-23 includes the preliminary steps of:
1) binding of the delivery vehicle via its Targeting Moiety (TM) to a a target cell; and
2) translocation of the modified BoNT/A L-chain into the the target cell, preferably into the cytosol of said target cell, via the translocation peptide of the delivery vehicle.

Preferably, the TM binds to a site on the target cell (e.g. to a protein, sugar, and/or lipid molecule), said site being capable of receptor-mediated endocytosis, and the delivery vehicle is subsequently internalised within the target cell via endosome formation. Thereafter, the translocation peptide of the delivery vehicle can translocate the modified BoNT/A L-chain across the endosomal membrane and into the cytosol of the target cell.

In another aspect, the invention relates to a modified (BoNT/A) L-chain protease, or to a nucleic acid construct, or to a delivery vehicle, as herein described, for use in a method of cleaving hSNAP23, as described above.

In another aspect, the present invention embraces a modified (BoNT/A) L-chain protease described herein for use in a method of treatment, preferably a method of treating a secretory disorder.

Thus, one aspect provides a BoNT/A L-chain protease described herein, or a nucleic acid construct described herein, or a delivery vehicle described herein for use as a medicament.

In such aspects, said modified (BoNT/A) L-chain protease is preferably comprised within a BoNT additionally comprising a heavy chain i.e. a full lenth BoNT. Such full length BoNTs typically have a 150 kDa polypeptide chain comprising a 100 kDa heavy chain and a 50 kDa light chain linked by a disulfide bond, and are organized into three functional domains: an N-terminal proteolytic light chain (L-chain); and a C-terminal heavy chain (H-chain), the latter consisting of a translocation domain ($H_N$) and a C-terminal neuron-binding domain ($H_C$).

Preferred secretory disorders include muscle spasticity/overactive muscle movement (including post-stroke spasticity, post-spinal cord injury spasticity, spasms of the head and neck, eyelid, vagina, limbs, jaw, and vocal cords), strabismus, hyperhidrosis, and severe primary axillary hyperhidrosis.

The present invention will be better understood in the light of the following detailed examples. Nevertheless, the skilled artisan will appreciate that this detailed description is not limitative and that various modifications, substitutions, omissions, and changes may be made without departing from the scope of the invention.

DESCRIPTION OF THE DRAWINGS

FIG. 1A depicts hSNAP-23 and hSNAP25 cleavage data for modified BoNT/A L-chain proteases of the present invention having mutations in a single binding pocket.

FIG. 1(B) depicts hSNAP-23 and hSNAP25 cleavage data for modified BoNT/A L-chain proteases of the present invention having mutations in multiple binding pockets.

FIG. 1(C) depicts hSNAP-23 and hSNAP25 cleavage data for modified BoNT/A L-chain proteases having mutations in a single binding pocket.

AMINO ACID SEQUENCES

Figure 2:
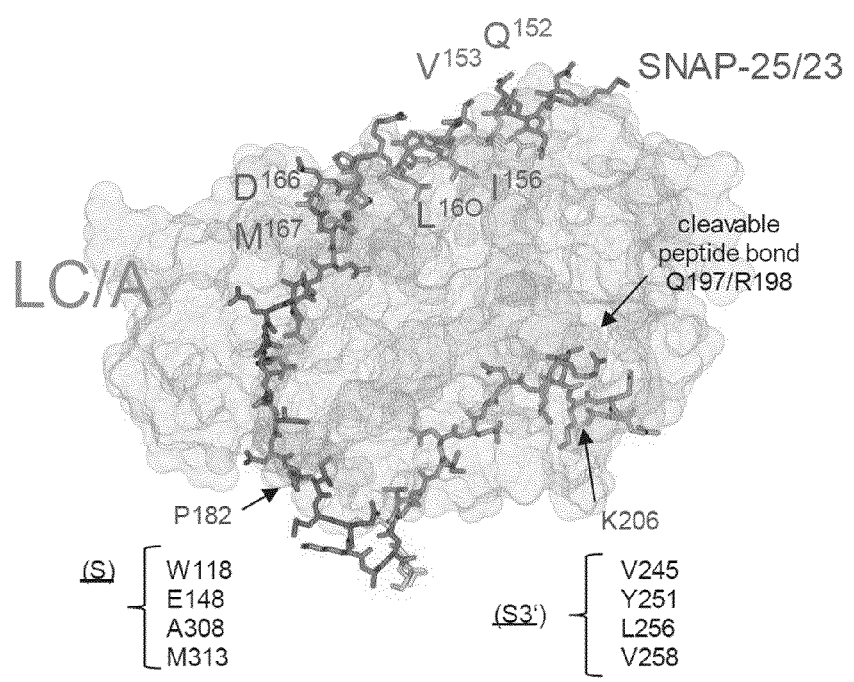
FIG. 2—A 3D rendered image of the BoNT/A L-chain protease (countour) interaction with binding pockets of SNAP-25/23 (line rendered).

```
SEQ ID NO: 1-wild-type BoNT/A light chain (amino
acid residues 1-438 of Uniprot A5HZZ9)
MPFVNKQFNYKDPVNGVDIAYIKIPNAGQMQPVKAFKIHNKIWVIPERDT
FTNPEEGDLNPPPEAKQVPVSYYDSTYLSTDNEKDNYLKGVTKLFERIYS
TDLGRMLLTSIVRGIPFWGGSTIDTELKVIDTNCINVIQPDGSYRSEELN
LVIIGPSADIIQFECKSFGHEVLNLTRNGYGSTQYIRFSPDFTFGFEESL
EVDTNPLLGAGKFATDPAVTLAHELIHAGHRLYGIAINPNRVFKVNTNAY
YEMSGLEVSFEELRTFGGHDAKFIDSLQENEFRLYYYNKFKDIASTLNKA
KSIVGTTASLQYMKNVFKEKYLLSEDTSGKFSVDKLKFDKLYKMLTEIYT
EDNFVKFFKVLNRKTYLNFDKAVFKINIVPKVNYTIYDGFNLRNTNLAAN
FNGQNTEINNMNFTKLKNFTGLFEFYKLLCVRGIITSK SEQ ID NO: 2-human SNAP23
MDNLSSEEIQQRAHQITDESLESTRRILGLAIESQDAGIKTITMLDEQKE
QLNRIEEGLDQINKDMRETEKTLTELNKCCGLCVCPCNRTKNFESGKAYK
TTWGDGGENSPCNVVSKQPGPVTNGQLQQPTTGAASGGYIKRITNDARED
EMEENLTQVGSILGNLKDMALNIGNEIDAQNPQIKRITDKADTNRDRIDI
ANARAKKLIDS SEQ ID NO: 3-human and rodent SNAP25
MAEDADMRNELEEMQRRADQLADESLESTRRMLQLVEESKDAGIRTLVML
DEQGEQLERIEEGMDQINKDMKEAEKNLTDLGKFCGLCVCPCNKLKSSDA
YKKAWGNNQDGVVASQPARVVDEREQMAISGGFIRRVTNDARENEMDENL
EQVSGIIGNLRHMALDMGNEIDTQNRQIDRIMEKADSNKTRIDEANQRAT
KMLGSG SEQ ID NO: 4-IgA-protease site His6Tag
(artificial)
PPTPGHHHHHH SEQ ID NO: 5-Twin Strep Tag (artificial)
MASWSHPQFEKGGGSGGGSGGGSWSHPQFEKGAGS SEQ ID NO: 6-His6 Tag (artificial)
GHHHHHH SEQ ID NO: 7-V-IgA-protease site His6Tag
(artificial)
VPPTPGHHHHHH SEQ ID NO: 8-wild-type BoNT/A1
MPFVNKQFNYKDPVNGVDIAYIKIPNAGQMQPVKAFKIHNKIWVIPERDT
FTNPEEGDLNPPPEAKQVPVSYYDSTYLSTDNEKDNYLKGVTKLFERIYS
TDLGRMLLTSIVRGIPFWGGSTIDTELKVIDTNCINVIQPDGSYRSEELN
LVIIGPSADIIQFECKSFGHEVLNLTRNGYGSTQYIRFSPDFTFGFEESL
EVDTNPLLGAGKFATDPAVTLAHELIHAGHRLYGIAINPNRVFKVNTNAY
YEMSGLEVSFEELRTFGGHDAKFIDSLQENEFRLYYYNKFKDIASTLNKA
KSIVGTTASLQYMKNVFKEKYLLSEDTSGKFSVDKLKFDKLYKMLTEIYT
EDNFVKFFKVLNRKTYLNFDKAVFKINIVPKVNYTIYDGFNLRNTNLAAN
FNGQNTEINNMNFTKLKNFTGLFEFYKLLCVRGIITSKTKSLDKGYNKAL
NDLCIKVNNWDLFFSPSEDNFTNDLNKGEEITSDTNIEAAEENISLDLIQ
QYYLTFNFDNEPENISIENLSSDIIGQLELMPNIERFPNGKKYELDKYTM
FHYLRAQEFEHGKSRIALTNSVNEALLNPSRVYTFFSSDYVKKVNKATEA
AMFLGWVEQLVYDFTDETSEVSTTDKIADITIIIPYIGPALNIGNMLYKD
DFVGALIFSGAVILLEFIPEIAIPVLGTFALVSYIANKVLTVQTIDNALS
KRNEKWDEVYKYIVTNWLAKVNTQIDLIRKKMKEALENQAEATKAIINYQ
YNQYTEEEKNNINFNIDDLSSKLNESINKAMININKFLNQCSVSYLMNSM
IPYGVKRLEDFDASLKDALLKYIYDNRGTLIGQVDRLKDKVNNTLSTDIP
FQLSKYVDNQRLLSTFTEYIKNIINTSILNLRYESNHLIDLSRYASKINI
GSKVNFDPIDKNQIQLFNLESSKIEVILKNAIVYNSMYENFSTSFWIRIP
KYFNSISLNNEYTIINCMENNSGWKVSLNYGEIIWTLQDTQEIKQRVVFK
YSQMINISDYINRWIFVTITNNRLNNSKIYINGRLIDQKPISNLGNIHAS
NNIMFKLDGCRDTHRYIWIKYFNLFDKELNEKEIKDLYDNQSNSGILKDF
WGDYLQYDKPYYMLNLYDPNKYVDVNNVGIRGYMYLKGPRGSVMTTNIYL
NSSLYRGTKFIIKKYASGNKDNIVRNNDRVYINVVVKNKEYRLATNASQA
GVEKILSALEIPDVGNLSQVVVMKSKNDQGITNKCKMNLQDNNGNDIGFI
GFHQFNNIAKLVASNWYNRQIERSSRTLGCSWEFIPVDDGWGERPL SEQ ID NO: 9-LH$_N$ linker (artificial)
VRGIITSKTKSLDKGYNKALNDL SEQ ID NO: 10-enterokinase activation site
DDDDK SEQ ID NO: 11-BoNT/A1 activation loop
VDGIITSKTKSDDDDKNKALNLQ
```

EXAMPLES

Example 1—Manufacture of Modified BoNT/A L-Chains (BoNT/A LC) According to the Invention Wild-type BoNT/A L-chain (amino acids 1-448, SEQ ID NO: 1) encoding plasmid, pBN3, was generated by PCR and suitable oligonucleotide primers using bacterial DNA of strain 62A as template. DNA encoding the amino acid sequence PPTPGHHHHHH (SEQ ID NO: 4) was inserted following the codon for amino acid Ala-449. The E. coli strain M15pREP4 (Qiagen, Hilden, Germany) was transfected with pBN3 containing the wt BoNT/A LC or with its mutants, i.e. with protease mutants of SEQ ID NO: 1 as described in the present application. For each transfected E. coli strain, a single bacterial colony grown overnight in 5 ml of 2YT medium was used to inoculate 500 ml 2YT medium. After the culture reached an OD600 of 0.7, BoNT/A L-chains were produced during 15 h of induction using 0.2 mM IPTG at 21° C. Bacteria were collected by centrifugation and frozen at −20° C. over night. Bacteria were resuspended in lysis buffer (300 mM NaCl, 50 mM phosphate, pH 8.0) supplemented with benzamidine, pepstatin A, and PMSF at final concentrations of 5 mM, 1 µg/ml, and 0.5 mM, respectively, lyzed by sonication, the lysate cleared by centrifugation for 30 minutes at 29.000 g, and BoNT/A L-chain bound to Ni2+-nitrilotri-acetic acid-agarose beads. Beads were washed with 20 bed volumes of lysis buffer containing 10 mM imidazole, and BoNT/A L-chain eluted by lysis buffer containing 100 mM imidazole. Fractions containing the desired protein were dialyzed against toxin assay buffer (150 mM potassium glutamate, 10 mM Hepes-KOH, pH 7.2), and the purified L-chain finally frozen in liquid nitrogen, and kept at −70° C.

Example 2—hSNAP-23 Cell-Free Cleavage Assay hSNAP-23 (SEQ ID NO: 2) plasmid for E. coli expression and in vitro transcription/translation, pS3-hSNAP-23His6, was generated.

It encodes an N-terminally fused twin strep-tag (MAS-WSHPQFEKGGGSGGGSGGGSWSHPQFEKGAGS, SEQ ID NO: 5) and a C-terminally fused His6-tag (GHHHHHH, SEQ ID NO: 6) downstream of the codon for carboxyl-terminal serine-211.

For protein production and purification, pS3-hSNAP-23His6 was transfected into the *E. coli* strain BL21-DE3 (Stratagene Europe, Ebsdorfergrund, Germany) and the same protocol was applied as detailed for BoNT/A L-chain protease in Example 1. However, protein eluted from the Ni2+-nitrilotri-acetic acid-agarose beads was further purified on Strep-Tactin agarose beads (IBA Lifesciences, Gottingen, Germany) by washing with 20 bed volumes of 0.1 M Tris pH 8.0 and elution with 10 mM desthiobiotin in 0.1 M Tris pH 8.0. In addition, all buffers used for hSNAP-23 purification were supplemented with 10 mM β-mercaptoethanol.

Radiolabled hSNAP-23 was subsequently generated by in vitro transcription/translation using pS3-hSNAP-23His6, the T7 coupled TNT reticulocyte lysate system (Promega), and [35S] methionine (370 KBq/µl, >37 TBq/mmol; Hartmann Analytic, Braunschweig, Germany) according to the manufacturer's instructions.

hSNAP-23 cell-free cleavage assay contained recombinant hSNAP-23 at a 20 micromolar final concentration plus 1 µl of transcription/translation mixture of [35S] methionine-labeled hSNAP-23 and each modified or wild-type BoNT/A L-chain at final concentrations of either 1 micromolar or 10 nanomolar, which was incubated for 60 min at 37° C. in a total volume of 10 µl of toxin assay buffer. Reactions were stopped by the addition of an equal volume of double-concentrated sample buffer [120 mM Tris-HCl (pH 6.75), 10% (v/v) β-mercaptoethanol, 4% (w/v) SDS, 20% (w/v) glycerol, and 0.014% (w/v) bromophenol blue]. After incubation for 30 min at 37° C., each sample was analyzed by SDS-PAGE using 15% Tris-glycine gels (acrylamide/bis-acrylamide ratio: 73.5:1).

Gels were dried and radiolabeled protein visualized employing a FLA-9000 phosphorimager (Fuji Photo Film, Co., Ltd., Tokyo, Japan). Quantification of radiolabeled protein and its cleavage products was performed with the Multigauge 3.2 software (Fuji Photo Film). For the determination of the enzyme kinetic parameters of wild-type BoNT/A L-chain and its mutants, the substrate concentration was varied between 5 and 100 µM employing hSNAP-23 produced in *E. coli*. Each of the various substrate concentrations was endowed by the addition of 1 µl of radiolabeled hSNAP-23 generated by in vitro transcription/translation. Incubation was performed in a final volume of 25 µl of toxin assay buffer. After 2 and 4 min of incubation at 37° C., aliquots of 10 µl were taken and the enzymatic reaction stopped by mixing with 10 µl of prechilled double-concentrated SDS-PAGE sample buffer. The percentage of cleavage was determined from the turnover of the radiolabeled substrate as detailed above and used to calculate the initial velocity of substrate hydrolysis. Km, Kcat and Vmax values were calculated by non-linear regression using the GraphPad Prism 4.03 program (GraphPad Software Inc., San Diego, USA).

The resulting data are shown in FIG. 1.

Example 3—hSNAP-25 Cell-Free Cleavage Assay hSNAP-25 (SEQ ID NO: 3) plasmid for *E. coli* expression (pBN10) has been described in Binz et al.(*J Biol Chem.*, 1994; 269:1617-20). The codon for the carboxyl-terminal glycine-206 is followed by DNA encoding the amino acid sequence VPPTPGHHHHHH (SEQ ID NO: 7). A plasmid for in vitro transcription/translation, pSNAP-25His6, was subsequently generated by subcloning the EcoRI-SalI fragment of pBN10 in pSP73 (Promega, Mannheim, Germany) cleaved correspondingly.

For protein production and purification of SNAP-25, pBN10 was transfected into the *E. coli* strain M15pREP4 (Qiagen, Hilden, Germany) and the same protocol was applied as detailed for BoNT/A L-chain protease in Example 1.

Radiolabled SNAP-25 was generated by in vitro transcription/translation using pSNAP-25His6, the SP6 coupled TNT reticulocyte lysate system (Promega), and [35S] methionine (370 KBq/µl, >37 TBq/mmol; Hartmann Analytic, Braunschweig, Germany) according to the manufacturer's instructions.

hSNAP25 cleavage assay was performed exactly as described for hSNAP-23 in Example 2.

The resulting data are shown in FIG. 1.

Example 4—Manufacture of $LH_N$ Domains Containing a Modified Light Chain A (BoNT/A LC) According to the Invention This Example describes the construction of translocation $LH_N$ domains containing a modified light chain A (BoNT/A LC) displaying hSNAP23 cleaving activity according to the invention. Such $LH_N$ domains can be used to create families of TSI delivery vehicles, by adding appropriate Targeting Moeities.

Briefly, BoNT/A LC cloning vectors were firstly constructed, for each mutant of the BoNT/A LC according to the invention, by chemically synthetizing DNA (GeneArt, ThermoFisher), that encodes said mutant BoNT/A LC and that is optimized for expression into *E. coli*, subcloned into the pCR 4 vector (Invitrogen). In parallel, a BoNT/A $H_N$ domain cloning vector was similarly constructed by chemically synthetizing codon-optimized DNA encoding $H_N$/A domain (corresponding to amino acid residues 449 to 872 of SEQ ID NO: 8, UniprotKB accession number A5HZZ9), subcloned into a standard vector, such as the pCR 4 vector (Invitrogen). A $LH_N$ linker cloning vector was further constructed by chemically synthetizing codon-optimized DNA encoding said linker subcloned into a standard vector, the pCR 4 vector (Invitrogen). In particular, the $LH_N$ linker VRGIITSKTKSLDKGYNKALNDL (SEQ ID NO: 9) which is suitable for the BoNT/A serotype (it is the inter-domain polypeptidic region that exists between the cysteines of the disulphide bridge between the LC and the $H_N$ domain of BoNT/A) was used for construction of the LH$_N$ linkervector. Alternative LH$_N$ linker constructs can be generated: indeed, as well-known to the skilled practitioner, for generation of a specific protease cleavage site, either the native suceptibility to proteolysis by the LysC protease can be used, or an enterokinase activation site (e.g. DDDDK, SEQ ID NO: 10) can be inserted into the activation loop to generate a sequence such as VDGIITSKTKSDDDDKNKALNLQ (SEQ ID NO: 11), or a protease site for any other protease well-known in the art, such as PreScision, Factor Xa, Thrombin, TEV protease, etc., can be inserted into the activation loop.

The LH$_N$ domains were subsequently assembled by cloning, in 2 main steps, the DNA encoding each of the modified BoNT/A LC of the invention upstream of the DNA encoding the LH$_N$ linker, said linker being further upstream of the DNA encoding the H$_N$/A domain, into a modified pET expression vector (Novagen).

Example 5—Manufacture of TSI Delivery Vehicles Binding to a Non-Neuronal Cell According to the Invention This Example describes the construction of TSI delivery vehicles by adding a suitable Targeting Moiety (herein, human GHRP) to each C-terminal end of the LH$_N$ domains containing a modified light chain A of the invention, as described in Example 2 above. To do so, a flexible linker was introduced between the Targeting Moiety and the LH$_N$ domain.

Briefly, linker-hGHRP cloning vectors were constructed by chemically synthetizing codon-optimized DNA encoding a flexible linker fused in frame to hGHRP Targeting Moeity, subcloned into the pCR 4 vector (Invitrogen).

The TSI constructs were subsequently assembled by cloning the DNA encoding the linker-hGHRP into each of the pET expression vectors containing the LH$_N$ domains described in Example 2, in such manner that the linker-hGHRP is fused in frame to the C-terminal end of each LH$_N$ domain.

For protein expression of each TSI vehicle, 100 ml of modified Terrific Broth (TB) medium containing 0.2% glucosamine and 30 µg/ml kanamycin in a 250 ml flask were incubated with a single bacterial colony (*E. coli* BL21 (DE3) transfected with the TSI. Each culture was grown at 37° C., 225 rpm for 16 hours; followed by inoculation of 1 L of modified TB containing 0.2% glucosamine and 30 µg/ml kanamycin in a 2 L flask with 10 ml of the overnight culture. The resulting culture was then grown at 37° C. until an approximate OD600 nm of 0.5 was reached at which point the temperature was reduced to 16° C. After 1 hour, each culture was induced with 1 mM IPTG and further grown at 16° C. for a further 16 hours. Bacteria were collected by centrifugation and frozen at −20° C. over night.

Subsequent purification of each expressed TSI was performed as follows.

Bacteria were defrosted and the cell pellet was sonicated to lyse the cells. After centrifugation, the supernatant was loaded onto a 0.1 M NiSO4 charged Chelating column equilibrated with 50 mM HEPES pH 7.2 200 mM NaCl. Washing of the column was performed with a buffer containing 40 to 100 mM imidazole (step gradient) to elute the non-bound protein, and with a buffer containing 200 mM imidazole to elute the TSI protein. Fractions containing the desired protein (TSI) were subsequently dialized against a buffer containing 50 mM HEPES pH 7.2 200 mM NaCl. The protease was then added (herein LysC) in an appropriate amount to 1 mg of the purified TSI to activate it (i.e. so that the TSI forms a di-chain, capable of binding to GHRP, translocating the light chain into the cytoplasm and of catalytically cleaving hSNAP23). The resulting mixture was then further purified by loading it to a 0.1 M NiSO4 charged Chelating column equilibrated with 50 mM HEPES pH 7.2 200 mM NaCl. The column was washed a first time with 50 mM HEPES pH 7.2 200 mM NaCl, then with a buffer containing 40 to 100 mM imidazole to elute the non-specific bound protein and with a buffer containing 200 mM imidazole to elute the activated TSI. Fractions containing the desired activated protein (TSI) were subsequently dialized against a buffer containing 50 mM HEPES pH 7.2 150 mM NaCl. The dialized protein was then concentrated to about 2 mg/ml, aliquoted and finally frozen at −80° C.

Clauses

1. A modified botulinum neurotoxin A (BoNT/A) L-chain protease that cleaves human SNAP-23 (hSNAP-23), and having a modified amino acid sequence relative to the wild-type BoNT/A L-chain (SEQ ID NO: 1), that comprises:
    a) at least one amino acid residue change located within a first BoNT/A L-chain protease binding pocket for binding to the P182/D178 binding site of hSNAP-23;
    b) wherein said first BoNT/A L-chain protease binding pocket is defined by amino acid residues E148, T307, A308 and Y312 of wild-type BoNT/A L-chain (SEQ ID NO: 1);
    c) and wherein said at least one amino acid residue change comprises:
        i. an amino acid residue selected from the group consisting of asparagine and tyrosine at the position on the modified L-chain protease amino acid sequence that corresponds to amino acid residue E148 of wild-type BoNT/A L-chain (SEQ ID NO: 1); and/ or
        ii. an amino acid residue selected from the group consisting of phenylalanine, isoleucine and leucine at the position on the modified L-chain protease amino acid sequence that corresponds to amino acid residue T307 of wild-type BoNT/A L-chain (SEQ ID NO: 1); and/ or
        iii. an amino acid residue selected from the group consisting of proline, asparagine, threonine and isoleucine at the position on the modified L-chain protease amino acid sequence that corresponds to amino acid residue A308 of wild-type BoNT/A L-chain (SEQ ID NO: 1); and/ or
        iv. an amino acid residue selected from the group consisting of lysine, valine, methionine and leucine at the position on the modified L-chain protease amino acid sequence that corresponds to amino acid residue Y312 of wild-type BoNT/A L-chain (SEQ ID NO: 1).

2. The modified BoNT/A L-chain protease according to clause 1, further comprising:
    a) an amino acid residue change located within a second BoNT/A L-chain protease binding pocket for binding to the R186 binding site of hSNAP-23;
    b) wherein said second BoNT/A L-chain protease binding pocket is defined by amino acid residue S143 of wild-type BoNT/A L-chain (SEQ ID NO: 1);
    c) and wherein said amino acid residue change comprises:
        i. an amino acid residue selected from the group consisting of glutamine, glutamate and aspartate at the position on the modified L-chain protease amino acid sequence that corresponds to amino acid residue S143 of wild-type BoNT/A L-chain (SEQ ID NO: 1).

3. The modified BoNT/A L-chain protease according to clause 1 or 2, further comprising:
   a) at least one amino acid residue change located within a third BoNT/A L-chain protease binding pocket for binding to the K185 binding site of hSNAP-23;
   b) wherein said third BoNT/A L-chain protease binding pocket is defined by amino acid residues V304 and G305 of wild-type BoNT/A L-chain (SEQ ID NO: 1);
   c) and wherein said at least one amino acid residue change comprises:
      i. an amino acid residue selected from the group consisting of glutamate and aspartate at the position on the modified L-chain protease amino acid sequence that corresponds to amino acid residue V304 of wild-type BoNT/A L-chain (SEQ ID NO: 1); and/ or
      ii. an amino acid residue selected from the group consisting of glutamate and aspartate at the position on the modified L-chain protease amino acid sequence that corresponds to amino acid residue G305 of wild-type BoNT/A L-chain (SEQ ID NO: 1).

4. The modified BoNT/ A L-chain protease according to any preceding clause, further comprising:
   a) an amino acid residue change located within a fourth BoNT/A L-chain protease binding pocket for binding to the D189/D192 binding site of hSNAP-23;
   b) wherein said fourth BoNT/A L-chain protease binding pocket is defined by amino acid residue Q29 of wild-type BoNT/A L-chain (SEQ ID NO: 1);
   c) and wherein said amino acid residue change comprises:
      i. an amino acid residue selected from the group consisting of alanine at the position on the modified L-chain protease amino acid sequence that corresponds to amino acid residue Q29 of wild-type BoNT/A L-chain (SEQ ID NO: 1).

5. The modified BoNT/ A L-chain protease according to any preceding clause, further comprising:
   a) at least one amino acid residue change located within a fifth BoNT/A L-chain protease binding pocket for binding to the K206 binding site of hSNAP-23;
   b) wherein said fifth BoNT/A L-chain protease binding pocket is defined by amino acid residue Y251, L256, V258, L367 and F369 of wild-type BoNT/A L-chain (SEQ ID NO: 1);
   c) and wherein said at least one amino acid residue change comprises:
      i. an amino acid residue selected from the group consisting of glutamate and aspartate at the position on the modified L-chain protease amino acid sequence that corresponds to amino acid residue Y251 of wild-type BoNT/A L-chain (SEQ ID NO: 1); and/ or
      ii. an amino acid residue selected from the group consisting of glutamate, aspartate, glutamine, glycine, alanine and arginine at the position on the modified L-chain protease amino acid sequence that corresponds to amino acid residue L256 of wild-type BoNT/A L-chain (SEQ ID NO: 1); and/ or
      iii. an amino acid residue selected from the group consisting of serine, alanine, proline, leucine and glutamate at the position on the modified L-chain protease amino acid sequence that corresponds to amino acid residue V258 of wild-type BoNT/A L-chain (SEQ ID NO: 1); and/ or
      iv. an amino acid residue selected from the group consisting of alanine and glycine at the position on the modified L-chain protease amino acid sequence that corresponds to amino acid residue L367 of wild-type BoNT/A L-chain (SEQ ID NO: 1); and/ or
      v. an amino acid residue selected from the group consisting of glycine, serine and leucine at the position on the modified L-chain protease amino acid sequence that corresponds to amino acid residue F369 of wild-type BoNT/A L-chain (SEQ ID NO: 1).

6. The modified BoNT/A L-chain protease according to any preceding clause, further comprising:
   a) an amino acid residue change located within a sixth BoNT/A L-chain protease binding pocket for binding to the 1198 binding site of hSNAP-23;
   b) wherein said sixth BoNT/A L-chain protease binding pocket is defined by amino acid residue K166 of wild-type BoNT/A L-chain (SEQ ID NO: 1);
   c) and wherein said amino acid residue change comprises:
      i. an amino acid residue selected from the group consisting of valine, phenylalanine, leucine and isoleucine at the position on the modified L-chain protease amino acid sequence that corresponds to amino acid residue K166 of wild-type BoNT/A L-chain (SEQ ID NO: 1).

7. The modified BoNT/A L-chain protease according to any preceding clause, further comprising:
   a) an amino acid residue change located within a seventh BoNT/A L-chain protease binding pocket for binding to the D210 binding site of hSNAP-23;
   b) wherein said seventh BoNT/A L-chain protease binding pocket is defined by amino acid residue S254 of wild-type BoNT/A L-chain (SEQ ID NO: 1);
   c) and wherein said amino acid residue change comprises:
      i. an amino acid residue selected from the group consisting of alanine at the position on the modified L-chain protease amino acid sequence that corresponds to amino acid residue S254 of wild-type BoNT/A L-chain (SEQ ID NO: 1).

8. The modified BoNT/A L-chain protease according to any preceding clause, further comprising:
   a) an amino acid residue change located within an eighth BoNT/A L-chain protease binding pocket for binding to the D168 binding site of hSNAP-23;
   b) wherein said eighth BoNT/A L-chain protease binding pocket is defined by amino acid residue K340 of wild-type BoNT/A L-chain (SEQ ID NO: 1);
   c) and wherein said amino acid residue change comprises:
      i. an amino acid residue selected from the group consisting of histidine at the position on the modified L-chain protease amino acid sequence that corresponds to amino acid residue K340 of wild-type BoNT/A L-chain (SEQ ID NO: 1).

9. A modified botulinum neurotoxin A (BoNT/A) L-chain protease that cleaves human SNAP-23 (hSNAP-23) and having a modified amino acid sequence relative to the wild-type BoNT/A L-chain) (SEQ ID NO: 1), that comprises:
   a) an amino acid residue change located within a fourth BoNT/A L-chain protease binding pocket for binding to the D189/D192 binding site of hSNAP-23;
   b) wherein said fourth BoNT/A L-chain protease binding pocket is defined by amino acid residue Q29 of wild-type BoNT/A L-chain (SEQ ID NO: 1);
   c) and wherein said amino acid residue change comprises:
      i. an amino acid residue selected from the group consisting of alanine at the position on the modified L-chain protease amino acid sequence that corresponds to amino acid residue Q29 of wild-type BoNT/A L-chain (SEQ ID NO: 1).

10. A modified botulinum neurotoxin A (BoNT/A) L-chain protease that cleaves human SNAP-23 (hSNAP-23), and having a modified amino acid sequence relative to the wild-type BoNT/A L-chain (SEQ ID NO: 1), that comprises:
   a) an amino acid residue change located within a sixth BoNT/A L-chain protease binding pocket for binding to the I198 binding site of hSNAP-23;
   b) wherein said sixth BoNT/A L-chain protease binding pocket is defined by amino acid residue K166 of wild-type BoNT/A L-chain (SEQ ID NO: 1);
   c) and wherein said amino acid residue change comprises:
      i. an amino acid residue selected from the group consisting of valine, phenylalanine, leucine and isoleucine at the position on the modified L-chain protease amino acid sequence that corresponds to amino acid residue K166 of wild-type BoNT/A L-chain (SEQ ID NO: 1).

11. A modified botulinum neurotoxin A (BoNT/A) L-chain protease that cleaves human SNAP-23 (hSNAP-23), and having a modified amino acid sequence relative to the wild-type BoNT/A L-chain (SEQ ID NO: 1), that comprises:
   a) at least one amino acid residue change located within a fifth BoNT/A L-chain protease binding pocket for binding to the K206 binding site of hSNAP-23;
   b) wherein said fifth BoNT/A L-chain protease binding pocket is defined by amino acid residues Y251, L256, V258, L367 and F369 of wild-type BoNT/A L-chain (SEQ ID NO: 1);
   c) and wherein said at least one amino acid residue change comprises:
      i. an amino acid residue selected from the group consisting of glutamate and aspartate at the position on the modified L-chain protease amino acid sequence that corresponds to amino acid residue Y251 of wild-type BoNT/A L-chain (SEQ ID NO: 1); and/ or
      ii. an amino acid residue selected from the group consisting of aspartate, glutamine, glycine, alanine and arginine at the position on the modified L-chain protease amino acid sequence that corresponds to amino acid residue L256 of wild-type BoNT/A L-chain (SEQ ID NO: 1); and/ or
      iii. an amino acid residue selected from the group consisting of serine, alanine, proline, leucine and glutamate at the position on the modified L-chain protease amino acid sequence that corresponds to amino acid residue V258 of wild-type BoNT/A L-chain (SEQ ID NO: 1); and/ or
      iv. an amino acid residue selected from the group consisting of alanine and glycine at the position on the modified L-chain protease amino acid sequence that corresponds to amino acid residue L367 of wild-type BoNT/A L-chain (SEQ ID NO: 1); and/ or
      v. an amino acid residue selected from the group consisting of glycine, serine and leucine at the position on the modified L-chain protease amino acid sequence that corresponds to amino acid residue F369 of wild-type BoNT/A L-chain (SEQ ID NO: 1).

12. A modified botulinum neurotoxin A (BoNT/A) L-chain protease that cleaves human SNAP-23 (hSNAP-23), and having a modified amino acid sequence relative to the wild-type BoNT/A L-chain (SEQ ID NO: 1), that comprises:
   a) an amino acid residue change located within a seventh BoNT/A L-chain protease binding pocket for binding to the D210 binding site of hSNAP-23;
   b) wherein said seventh BoNT/A L-chain protease binding pocket is defined by amino acid residue S254 of wild-type BoNT/A L-chain (SEQ ID NO: 1);
   c) and wherein said amino acid residue change comprises:
      i. an amino acid residue selected from the group consisting of alanine at the position on the modified L-chain protease amino acid sequence that corresponds to amino acid residue S254 of wild-type BoNT/A L-chain (SEQ ID NO: 1).

13. A modified botulinum neurotoxin A (BoNT/A) L-chain protease that cleaves human SNAP-23 (hSNAP-23), and having a modified amino acid sequence relative to the wild-type BoNT/A L-chain (SEQ ID NO: 1), that comprises:
   a) an amino acid residue change located within an eighth BoNT/A L-chain protease binding pocket for binding to the D168 binding site of hSNAP-23;
   b) wherein said eighth BoNT/A L-chain protease binding pocket is defined by amino acid residue K340 of wild-type BoNT/A L-chain (SEQ ID NO: 1);
   c) and wherein said amino acid residue change comprises:
      i. an amino acid residue selected from the group consisting of histidine at the position on the modified L-chain protease amino acid sequence that corresponds to amino acid residue K340 of wild-type BoNT/A L-chain (SEQ ID NO: 1).

14. The modified botulinum neurotoxin A (BoNT/A) L-chain protease according to any of Clauses 9 to 13, further comprising at least one amino acid residue change located within a different BoNT/A L-chain protease binding pocket, wherein said amino acid residue change and said another BoNT/A L-chain protease binding pocket are defined by the technical features recited in any one of Clauses 1 to 13.

15. A nucleic acid construct comprising or consisting of a nucleic acid sequence encoding the modified BoNT/A L-chain protease as defined in any preceding Clause.

16. A delivery vehicle, comprising:
   a) the modified BoNT/A L chain protease as defined in any Clauses 1 to 14, or the nucleic acid construct of Clause 15; and
   b) means for delivering said modified BoNT/A L chain protease, or said nucleic acid construct, into a target cell, preferably into a non-neuronal target cell.

17. The delivery vehicle according to Clause 16, wherein the means b) for delivering said modified BoNT/A L chain protease to a target cell comprises:
   i) a targeting moiety that binds the delivery vehicle to the target cell; and
   ii) a translocation peptide that translocates the modified BoNT/A L-chain protease or the nucleic acid construct into the target cell, preferably into a non-neuronal target cell.

18. A method of cleaving hSNAP-23, comprising contacting hSNAP-23 with a (BoNT/A) L-chain protease according to any of Clauses 1 to 14, or with a nucleic acid construct according to Clause 15, or with a delivery vehicle according to Clause 16 or 17.

19. A (BoNT/A) L-chain protease according to any of Clauses 1 to 14, or a nucleic acid construct according to Clause 15, or a delivery vehicle according to Clause 16 or 17, for use in a method according to Clause 18.

The invention claimed is:

1. A modified botulinum neurotoxin A (BoNT/A) L-chain protease comprising an amino acid sequence that has at least 95% sequence identity to SEQ ID NO: 1 and
tyrosine at the position corresponding to residue position 148 of SEQ ID NO: 1.

2. The modified BoNT/A L-chain protease of claim 1, comprising alanine at the position corresponding to residue position 29 of SEQ ID NO: 1.

3. The modified BoNT/A L-chain protease of claim 1, comprising valine at the position corresponding to residue position 166 of SEQ ID NO: 1.

4. The modified BoNT/A L-chain protease of claim 1, comprising glutamate or aspartate at the position corresponding to residue position 305 of SEQ ID NO: 1.

5. The modified BoNT/A L-chain protease of claim 1, comprising glutamine, glutamate, or aspartate at the position corresponding to residue position 143 of SEQ ID NO: 1.

6. The modified BoNT/A L-chain protease of claim 1, comprising glutamate or aspartate at the position corresponding to residue position 251 of SEQ ID NO: 1.

7. A delivery vehicle, comprising:
a) the protease of claim 1; and
b) a means for delivering the protease into a target cell.

8. The delivery vehicle of claim 7, wherein the means for delivering the protease to the target cell comprises:
a) a targeting moiety that binds the delivery vehicle to the target cell; and
b) a translocation peptide that translocates the protease into the target cell.

9. A method of cleaving hSNAP-23, comprising contacting the hSNAP-23 with the protease of claim 1.

10. The delivery vehicle of claim 7, comprising a means for delivering the protease into a non-neuronal target cell.

11. The delivery vehicle of claim 8, wherein the target cell is a non-neuronal target cell.

12. A method of cleaving hSNAP-23, comprising contacting the hSNAP-23 with the protease of claim 7.

13. The protease of claim 1, wherein the amino acid sequence has at least 98% sequence identity to SEQ ID NO: 1.

14. The protease of claim 1, wherein the amino acid sequence has at least 99% sequence identity to SEQ ID NO: 1.

15. The protease of claim 1, wherein the amino acid sequence differs from SEQ ID NO: 1 by conservative amino acid substitutions and/or:
(a) having tyrosine at the position corresponding to residue position 148 of SEQ ID NO: 1;
(b) having tyrosine at the position corresponding to residue position 148 of SEQ ID NO: 1 and lysine at the position corresponding to position 312 of SEQ ID NO: 1;
(c) having tyrosine at the position corresponding to residue position 148 of SEQ ID NO: 1, phenylalanine at the position corresponding to position 307 of SEQ ID NO: 1, asparagine at the position corresponding to position 308 of SEQ ID NO: 1, and leucine at the position corresponding to 312 of SEQ ID NO: 1;
(d) having tyrosine at the position corresponding to residue position 148 of SEQ ID NO: 1, isoleucine at the position corresponding to position 307 of SEQ ID NO: 1, proline at the position corresponding to position 308 of SEQ ID NO: 1, and valine at the position corresponding to 312 of SEQ ID NO: 1;
(e) having tyrosine at the position corresponding to residue position 148 of SEQ ID NO: 1, leucine at the position corresponding to position 307 of SEQ ID NO: 1, tyrosine at the position corresponding to position 308 of SEQ ID NO: 1, and methionine at the position corresponding to 312 of SEQ ID NO: 1;
(f) having tyrosine at the position corresponding to residue position 148 of SEQ ID NO: 1, leucine at the position corresponding to position 307 of SEQ ID NO: 1, isoleucine at the position corresponding to position 308 of SEQ ID NO: 1, and methionine at the position corresponding to 312 of SEQ ID NO: 1;
(g) having tyrosine at the position corresponding to residue position 148 of SEQ ID NO: 1 and aspartic acid, glutamic acid, or glutamine at the position corresponding to residue position 143 of SEQ ID NO: 1;
(h) having tyrosine at the position corresponding to residue position 148 of SEQ ID NO: 1 and aspartic acid at the position corresponding to residue position 305 of SEQ ID NO: 1;
(i) having tyrosine at the position corresponding to residue position 148 of SEQ ID NO: 1 and alanine at the position corresponding to residue position 29 of SEQ ID NO: 1;
(j) having tyrosine at the position corresponding to residue position 148 of SEQ ID NO: 1, alanine at the position corresponding to residue position 29 of SEQ ID NO: 1, and aspartic acid at the position corresponding to residue position 143 of SEQ ID NO: 1;
(k) having tyrosine at the position corresponding to residue position 148 of SEQ ID NO: 1, alanine at the position corresponding to residue position 29 of SEQ ID NO: 1, and aspartic acid at the position corresponding to residue position 305 of SEQ ID NO: 1;
(l) having tyrosine at the position corresponding to residue position 148 of SEQ ID NO: 1 and aspartic acid or glutamic acid at the position corresponding to residue position 251 of SEQ ID NO: 1;
(m) having tyrosine at the position corresponding to residue position 148 of SEQ ID NO: 1 and aspartic acid at the position corresponding to residue position 256 of SEQ ID NO: 1;

(n) having tyrosine at the position corresponding to residue position 148 of SEQ ID NO: 1, alanine at the position corresponding to residue position 29 of SEQ ID NO: 1, aspartic acid at the position corresponding to residue position 143 of SEQ ID NO: 1, and glutamic acid at the position corresponding to residue position 251 of SEQ ID NO: 1;

(o) having tyrosine at the position corresponding to residue position 148 of SEQ ID NO: 1, phenylalanine or valine at the position corresponding to residue position 166 of SEQ ID NO: 1, and aspartic acid at the position corresponding to residue position 305 of SEQ ID NO: 1;

(p) having tyrosine at the position corresponding to residue position 148 of SEQ ID NO: 1, aspartic acid at the position corresponding to residue position 143 of SEQ ID NO: 1, and phenylalanine at the position corresponding to residue position 166 of SEQ ID NO: 1;

(q) having tyrosine at the position corresponding to residue position 148 of SEQ ID NO: 1, alanine at the position corresponding to residue position 29 of SEQ ID NO: 1, phenylalanine or valine at the position corresponding to residue position 166 of SEQ ID NO: 1, and aspartic acid at the position corresponding to residue position 305 of SEQ ID NO: 1;

(r) having tyrosine at the position corresponding to residue position 148 of SEQ ID NO: 1, alanine at the position corresponding to residue position 29 of SEQ ID NO: 1, phenylalanine or valine at the position corresponding to residue position 166 of SEQ ID NO: 1, glutamic acid at the position corresponding to residue position 251 of SEQ ID NO: 1, and aspartic acid at the position corresponding to residue position 305 of SEQ ID NO: 1;

(s) having tyrosine at the position corresponding to residue position 148 of SEQ ID NO: 1 and phenylalanine at residue position 166 of SEQ ID NO: 1;

(t) having tyrosine at the position corresponding to residue position 148 of SEQ ID NO: 1, phenylalanine at residue position 166 of SEQ ID NO: 1, and alanine at residue position 254 of SEQ ID NO: 1;

(u) having tyrosine at the position corresponding to residue position 148 of SEQ ID NO: 1, phenylalanine at residue position 166 of SEQ ID NO: 1, alanine at residue position 254 of SEQ ID NO: 1, and aspartic acid at residue position 305 of SEQ ID NO: 1; or (v) having tyrosine at the position corresponding to residue position 148 of SEQ ID NO: 1 and histidine at residue position 340 of SEQ ID NO: 1.

16. The protease of claim 1, wherein the amino acid sequence differs from SEQ ID NO: 1 by:

(a) having tyrosine at the position corresponding to residue position 148 of SEQ ID NO: 1;

(b) having tyrosine at the position corresponding to residue position 148 of SEQ ID NO: 1 and lysine at the position corresponding to 312 of SEQ ID NO: 1;

(c) having tyrosine at the position corresponding to residue position 148 of SEQ ID NO: 1, phenylalanine at the position corresponding to position 307 of SEQ ID NO: 1, asparagine at the position corresponding to position 308 of SEQ ID NO: 1, and leucine at the position corresponding to position 312 of SEQ ID NO: 1;

(d) having tyrosine at the position corresponding to residue position 148 of SEQ ID NO: 1, isoleucine at the position corresponding to position 307 of SEQ ID NO: 1, proline at the position corresponding to position 308 of SEQ ID NO: 1, and valine at the position corresponding to 312 of SEQ ID NO: 1;

(e) having tyrosine at the position corresponding to residue position 148 of SEQ ID NO: 1, leucine at the position corresponding to position 307 of SEQ ID NO: 1, tyrosine at the position corresponding to position 308 of SEQ ID NO: 1, and methionine at the position corresponding to 312 of SEQ ID NO: 1;

(f) having tyrosine at the position corresponding to residue position 148 of SEQ ID NO: 1, leucine at the position corresponding to position 307 of SEQ ID NO: 1, isoleucine at the position corresponding to position 308 of SEQ ID NO: 1, and methionine at the position corresponding to 312 of SEQ ID NO: 1;

(g) having tyrosine at the position corresponding to residue position 148 of SEQ ID NO: 1 and aspartic acid, glutamic acid, or glutamine at the position corresponding to residue position 143 of SEQ ID NO: 1;

(h) having tyrosine at the position corresponding to residue position 148 of SEQ ID NO: 1 and aspartic acid at the position corresponding to residue position 305 of SEQ ID NO: 1;

(i) having tyrosine at the position corresponding to residue position 148 of SEQ ID NO: 1 and alanine at the position corresponding to residue position 29 of SEQ ID NO: 1;

(j) having tyrosine at the position corresponding to residue position 148 of SEQ ID NO: 1, alanine at the position corresponding to residue position 29 of SEQ ID NO: 1, and aspartic acid at the position corresponding to residue position 143 of SEQ ID NO: 1;

(k) having tyrosine at the position corresponding to residue position 148 of SEQ ID NO: 1, alanine at the position corresponding to residue position 29 of SEQ ID NO: 1, and aspartic acid at the position corresponding to residue position 305 of SEQ ID NO: 1;

(l) having tyrosine at the position corresponding to residue position 148 of SEQ ID NO: 1 and aspartic acid or glutamic acid at the position corresponding to residue position 251 of SEQ ID NO: 1;

(m) having tyrosine at the position corresponding to residue position 148 of SEQ ID NO: 1 and aspartic acid at the position corresponding to residue position 256 of SEQ ID NO: 1;

(n) having tyrosine at the position corresponding to residue position 148 of SEQ ID NO: 1, alanine at the position corresponding to residue position 29 of SEQ ID NO: 1, aspartic acid at the position corresponding to residue position 143 of SEQ ID NO: 1, and glutamic acid at the position corresponding to residue position 251 of SEQ ID NO: 1;

(o) having tyrosine at the position corresponding to residue position 148 of SEQ ID NO: 1, phenylalanine or valine at the position corresponding to residue position 166 of SEQ ID NO: 1, and aspartic acid at the position corresponding to residue position 305 of SEQ ID NO: 1;

(p) having tyrosine at the position corresponding to residue position 148 of SEQ ID NO: 1, aspartic acid at the position corresponding to residue position 143 of SEQ ID NO: 1, and phenylalanine at the position corresponding to residue position 166 of SEQ ID NO: 1;

(q) having tyrosine at the position corresponding to residue position 148 of SEQ ID NO: 1, alanine at the position corresponding to residue position 29 of SEQ ID NO: 1, phenylalanine or valine at the position corresponding to residue position 166 of SEQ ID NO:

1, and aspartic acid at the position corresponding to residue position 305 of SEQ ID NO: 1;

(r) having tyrosine at the position corresponding to residue position 148 of SEQ ID NO: 1, alanine at the position corresponding to residue position 29 of SEQ ID NO: 1, phenylalanine or valine at the position corresponding to residue position 166 of SEQ ID NO: 1, glutamic acid at the position corresponding to residue position 251 of SEQ ID NO: 1, and aspartic acid at the position corresponding to residue position 305 of SEQ ID NO: 1;

(s) having tyrosine at the position corresponding to residue position 148 of SEQ ID NO: 1 and phenylalanine at residue position 166 of SEQ ID NO: 1;

(t) having tyrosine at the position corresponding to residue position 148 of SEQ ID NO: 1, phenylalanine at residue position 166 of SEQ ID NO: 1, and alanine at residue position 254 of SEQ ID NO: 1;

(u) having tyrosine at the position corresponding to residue position 148 of SEQ ID NO: 1, phenylalanine at residue position 166 of SEQ ID NO: 1, alanine at residue position 254 of SEQ ID NO: 1, and aspartic acid at residue position 305 of SEQ ID NO: 1; or (v) having tyrosine at the position corresponding to residue position 148 of SEQ ID NO: 1 and histidine at residue position 340 of SEQ ID NO: 1.

17. The protease of claim 1, wherein the amino acid sequence differs from SEQ ID NO: 1 by conservative amino acid substitutions and by having tyrosine at the position corresponding to residue position 148 of SEQ ID NO: 1.

18. The protease of claim 1, wherein the amino acid sequence differs from SEQ ID NO: 1 by having tyrosine at the position corresponding to residue position 148 of SEQ ID NO: 1.

* * * * *

SEQUENCE LISTING

<160> NUMBER OF SEQ ID NOS: 12

<210> SEQ ID NO 1
<211> LENGTH: 438
<212> TYPE: PRT
<213> ORGANISM: Clostridium botulinum

<400> SEQUENCE: 1

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365
```

```
Phe Asp Lys Ala Val Phe Lys Ile Asn Ile Val Pro Lys Val Asn Tyr
        370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
            420                 425                 430
Gly Ile Ile Thr Ser Lys
        435

<210> SEQ ID NO 2
<211> LENGTH: 211
<212> TYPE: PRT
<213> ORGANISM: Homo sapiens

<400> SEQUENCE: 2

Met Asp Asn Leu Ser Ser Glu Glu Ile Gln Gln Arg Ala His Gln Ile
1               5                   10                  15
Thr Asp Glu Ser Leu Glu Ser Thr Arg Arg Ile Leu Gly Leu Ala Ile
            20                  25                  30
Glu Ser Gln Asp Ala Gly Ile Lys Thr Ile Thr Met Leu Asp Glu Gln
        35                  40                  45
Lys Glu Gln Leu Asn Arg Ile Glu Glu Gly Leu Asp Gln Ile Asn Lys
    50                  55                  60
Asp Met Arg Glu Thr Glu Lys Thr Leu Thr Glu Leu Asn Lys Cys Cys
65                  70                  75                  80
Gly Leu Cys Val Cys Pro Cys Asn Arg Thr Lys Asn Phe Glu Ser Gly
                85                  90                  95
Lys Ala Tyr Lys Thr Thr Trp Gly Asp Gly Gly Glu Asn Ser Pro Cys
            100                 105                 110
Asn Val Val Ser Lys Gln Pro Gly Pro Val Thr Asn Gly Gln Leu Gln
        115                 120                 125
Gln Pro Thr Thr Gly Ala Ala Ser Gly Gly Tyr Ile Lys Arg Ile Thr
    130                 135                 140
Asn Asp Ala Arg Glu Asp Glu Met Glu Glu Asn Leu Thr Gln Val Gly
145                 150                 155                 160
Ser Ile Leu Gly Asn Leu Lys Asp Met Ala Leu Asn Ile Gly Asn Glu
                165                 170                 175
Ile Asp Ala Gln Asn Pro Gln Ile Lys Arg Ile Thr Asp Lys Ala Asp
            180                 185                 190
Thr Asn Arg Asp Arg Ile Asp Ile Ala Asn Ala Arg Ala Lys Lys Leu
        195                 200                 205
Ile Asp Ser
    210

<210> SEQ ID NO 3
<211> LENGTH: 206
<212> TYPE: PRT
<213> ORGANISM: Homo sapiens

<400> SEQUENCE: 3

Met Ala Glu Asp Ala Asp Met Arg Asn Glu Leu Glu Glu Met Gln Arg
1               5                   10                  15
Arg Ala Asp Gln Leu Ala Asp Glu Ser Leu Glu Ser Thr Arg Arg Met
            20                  25                  30
```

```
Leu Gln Leu Val Glu Glu Ser Lys Asp Ala Gly Ile Arg Thr Leu Val
         35                  40                  45

Met Leu Asp Glu Gln Gly Glu Gln Leu Glu Arg Ile Glu Glu Gly Met
 50                  55                  60

Asp Gln Ile Asn Lys Asp Met Lys Glu Ala Glu Lys Asn Leu Thr Asp
 65                  70                  75                  80

Leu Gly Lys Phe Cys Gly Leu Cys Val Cys Pro Cys Asn Lys Leu Lys
                 85                  90                  95

Ser Ser Asp Ala Tyr Lys Lys Ala Trp Gly Asn Asn Gln Asp Gly Val
                100                 105                 110

Val Ala Ser Gln Pro Ala Arg Val Val Asp Glu Arg Glu Gln Met Ala
            115                 120                 125

Ile Ser Gly Gly Phe Ile Arg Arg Val Thr Asn Asp Ala Arg Glu Asn
130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
            195                 200                 205

<210> SEQ ID NO 4
<211> LENGTH: 11
<212> TYPE: PRT
<213> ORGANISM: Artificial Sequence
<220> FEATURE:
<223> OTHER INFORMATION: IgA-protease site His6Tag

<400> SEQUENCE: 4

Pro Pro Thr Pro Gly His His His His His His
1               5                   10

<210> SEQ ID NO 5
<211> LENGTH: 35
<212> TYPE: PRT
<213> ORGANISM: Artificial Sequence
<220> FEATURE:
<223> OTHER INFORMATION: Twin Strep Tag

<400> SEQUENCE: 5

Met Ala Ser Trp Ser His Pro Gln Phe Glu Lys Gly Gly Gly Ser Gly
1               5                   10                  15

Gly Gly Ser Gly Gly Gly Ser Trp Ser His Pro Gln Phe Glu Lys Gly
            20                  25                  30

Ala Gly Ser
        35

<210> SEQ ID NO 6
<211> LENGTH: 7
<212> TYPE: PRT
<213> ORGANISM: Artificial Sequence
<220> FEATURE:
<223> OTHER INFORMATION: His6 Tag

<400> SEQUENCE: 6

Gly His His His His His His
1               5
```

-continued

```
<210> SEQ ID NO 7
<211> LENGTH: 12
<212> TYPE: PRT
<213> ORGANISM: Artificial Sequence
<220> FEATURE:
<223> OTHER INFORMATION: V-IgA-protease site His6Tag

<400> SEQUENCE: 7

Val Pro Pro Thr Pro Gly His His His His His His
1               5                   10

<210> SEQ ID NO 8
<211> LENGTH: 1296
<212> TYPE: PRT
<213> ORGANISM: Clostridium botulinum

<400> SEQUENCE: 8

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320
```

```
Tyr Leu Leu Ser Glu Asp Thr Ser Gly Lys Phe Ser Val Asp Lys Leu
            325                 330                 335

Lys Phe Asp Lys Leu Tyr Lys Met Leu Thr Glu Ile Tyr Thr Glu Asp
            340                 345                 350

Asn Phe Val Lys Phe Lys Val Leu Asn Arg Lys Thr Tyr Leu Asn
            355                 360             365

Phe Asp Lys Ala Val Phe Lys Ile Asn Ile Val Pro Lys Val Asn Tyr
            370                 375             380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
            405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
            435                 440                 445

Ala Leu Asn Asp Leu Cys Ile Lys Val Asn Asn Trp Asp Leu Phe Phe
            450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Asn Ile Ser Leu
            485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
            515                 520                 525

Glu Leu Met Pro Asn Ile Glu Arg Phe Pro Asn Gly Lys Lys Tyr Glu
            530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
            565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
            595                 600                 605

Gln Leu Val Tyr Asp Phe Thr Asp Glu Thr Ser Glu Val Ser Thr Thr
            610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
            645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
            675                 680                 685

Val Leu Thr Val Gln Thr Ile Asp Asn Ala Leu Ser Lys Arg Asn Glu
            690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
            725                 730                 735
```

-continued

Glu Asn Gln Ala Glu Ala Thr Lys Ala Ile Ile Asn Tyr Gln Tyr Asn
                740                 745                 750

Gln Tyr Thr Glu Glu Lys Asn Asn Ile Asn Phe Asn Ile Asp Asp
            755                 760                 765

Leu Ser Ser Lys Leu Asn Glu Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
                820                 825                 830

Gln Val Asp Arg Leu Lys Asp Lys Val Asn Asn Thr Leu Ser Thr Asp
                835                 840                 845

Ile Pro Phe Gln Leu Ser Lys Tyr Val Asp Asn Gln Arg Leu Leu Ser
                850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
                900                 905                 910

Gln Ile Gln Leu Phe Asn Leu Glu Ser Ser Lys Ile Glu Val Ile Leu
                915                 920                 925

Lys Asn Ala Ile Val Tyr Asn Ser Met Tyr Glu Asn Phe Ser Thr Ser
                930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
                980                 985                 990

Ile Lys Gln Arg Val Val Phe Lys Tyr Ser Gln Met Ile Asn Ile Ser
                995                 1000                1005

Asp Tyr Ile Asn Arg Trp Ile Phe Val Thr Ile Thr Asn Asn Arg
            1010                1015                1020

Leu Asn Asn Ser Lys Ile Tyr Ile Asn Gly Arg Leu Ile Asp Gln
            1025                1030                1035

Lys Pro Ile Ser Asn Leu Gly Asn Ile His Ala Ser Asn Asn Ile
            1040                1045                1050

Met Phe Lys Leu Asp Gly Cys Arg Asp Thr His Arg Tyr Ile Trp
            1055                1060                1065

Ile Lys Tyr Phe Asn Leu Phe Asp Lys Glu Leu Asn Glu Lys Glu
            1070                1075                1080

Ile Lys Asp Leu Tyr Asp Asn Gln Ser Asn Ser Gly Ile Leu Lys
            1085                1090                1095

Asp Phe Trp Gly Asp Tyr Leu Gln Tyr Asp Lys Pro Tyr Tyr Met
            1100                1105                1110

Leu Asn Leu Tyr Asp Pro Asn Lys Tyr Val Asp Val Asn Asn Val
            1115                1120                1125

Gly Ile Arg Gly Tyr Met Tyr Leu Lys Gly Pro Arg Gly Ser Val
            1130                1135                1140

Met Thr Thr Asn Ile Tyr Leu Asn Ser Ser Leu Tyr Arg Gly Thr
1145 1150 1155

Lys Phe Ile Ile Lys Lys Tyr Ala Ser Gly Asn Lys Asp Asn Ile
1160 1165 1170

Val Arg Asn Asn Asp Arg Val Tyr Ile Asn Val Val Val Lys Asn
1175 1180 1185

Lys Glu Tyr Arg Leu Ala Thr Asn Ala Ser Gln Ala Gly Val Glu
1190 1195 1200

Lys Ile Leu Ser Ala Leu Glu Ile Pro Asp Val Gly Asn Leu Ser
1205 1210 1215

Gln Val Val Val Met Lys Ser Lys Asn Asp Gln Gly Ile Thr Asn
1220 1225 1230

Lys Cys Lys Met Asn Leu Gln Asp Asn Asn Gly Asn Asp Ile Gly
1235 1240 1245

Phe Ile Gly Phe His Gln Phe Asn Asn Ile Ala Lys Leu Val Ala
1250 1255 1260

Ser Asn Trp Tyr Asn Arg Gln Ile Glu Arg Ser Ser Arg Thr Leu
1265 1270 1275

Gly Cys Ser Trp Glu Phe Ile Pro Val Asp Asp Gly Trp Gly Glu
1280 1285 1290

Arg Pro Leu
1295

<210> SEQ ID NO 9
<211> LENGTH: 23
<212> TYPE: PRT
<213> ORGANISM: Artificial Sequence
<220> FEATURE:
<223> OTHER INFORMATION: LHN linker

<400> SEQUENCE: 9

Val Arg Gly Ile Ile Thr Ser Lys Thr Lys Ser Leu Asp Lys Gly Tyr
1 5 10 15

Asn Lys Ala Leu Asn Asp Leu
20

<210> SEQ ID NO 10
<211> LENGTH: 5
<212> TYPE: PRT
<213> ORGANISM: Homo sapiens

<400> SEQUENCE: 10

Asp Asp Asp Asp Lys
1 5

<210> SEQ ID NO 11
<211> LENGTH: 23
<212> TYPE: PRT
<213> ORGANISM: Artificial Sequence
<220> FEATURE:
<223> OTHER INFORMATION: Modified BoNT/A1 activation loop

<400> SEQUENCE: 11

Val Asp Gly Ile Ile Thr Ser Lys Thr Lys Ser Asp Asp Asp Asp Lys
1 5 10 15

Asn Lys Ala Leu Asn Leu Gln
20

```
<210> SEQ ID NO 12
<211> LENGTH: 23
<212> TYPE: PRT
<213> ORGANISM: Influenza A virus

<400> SEQUENCE: 12

Gly Leu Phe Gly Ala Ile Ala Gly Phe Ile Glu Asn Gly Trp Glu Gly
1               5                   10                  15

Met Ile Asp Gly Trp Tyr Gly
            20
```